(12) United States Patent
Moelsgaard

(10) Patent No.: US 6,663,386 B1
(45) Date of Patent: Dec. 16, 2003

(54) DENTAL SYSTEM FOR TREATMENT OF PERIODONTAL POCKETS LASER LIGHT

(76) Inventor: Eigil Moelsgaard, Skodsborg Strandvej 300, DK-2942 Skodsborg (DK)

(*) Notice: Subject to any disclaimer, the term of this patent is extended or adjusted under 35 U.S.C. 154(b) by 0 days.

(21) Appl. No.: 09/601,456

(22) PCT Filed: Feb. 8, 1999

(86) PCT No.: PCT/DK99/00057

§ 371 (c)(1),
(2), (4) Date: Aug. 2, 2000

(87) PCT Pub. No.: WO99/39652

PCT Pub. Date: Aug. 12, 1999

(30) Foreign Application Priority Data

Feb. 6, 1998 (DK) .................................. 0179/98
May 12, 1998 (DK) .................................. 0651/98

(51) Int. Cl.⁷ ................................................ A61C 1/07
(52) U.S. Cl. ...................................... 433/29; 433/215
(58) Field of Search .................... 433/29, 215; 606/10, 606/15, 16

(56) References Cited

U.S. PATENT DOCUMENTS

| | | | | |
|---|---|---|---|---|
| 4,826,431 A | * | 5/1989 | Fujimura et al. | 433/215 |
| 5,318,562 A | * | 6/1994 | Levy et al. | 606/13 |
| 5,324,200 A | | 6/1994 | Vassiliadis et al. | 433/224 |
| 5,374,266 A | * | 12/1994 | Kataoka et al. | 604/21 |
| 5,437,662 A | | 8/1995 | Nardella | 606/40 |
| 5,636,983 A | * | 6/1997 | Shoji et al. | 433/29 |
| 5,785,521 A | * | 7/1998 | Rizoiu et al. | 433/104 |
| 5,846,080 A | * | 12/1998 | Schneider | 433/215 |
| 6,039,565 A | * | 3/2000 | Chou et al. | 433/119 |
| 6,129,721 A | * | 10/2000 | Kataoka et al. | 606/16 |
| 6,162,052 A | * | 12/2000 | Kokubu | 433/224 |

FOREIGN PATENT DOCUMENTS

| | | |
|---|---|---|
| DE | A1-4138468 | 6/1993 |
| DE | A1-4239829 | 6/1993 |
| EP | A2164751 | 12/1985 |

OTHER PUBLICATIONS

Visuri et al.; Lasers in Surgery and Medicine, vol. 18, No. 3, pp. 296–300 (1996).

* cited by examiner

Primary Examiner—Cary E. O'Connor
(74) Attorney, Agent, or Firm—Birch, Stewart, Kolasch & Birch, LLP

(57) ABSTRACT

A dental system for treatment of periodontal pockets using laser light, comprising a handpiece for directing laser light and a coolant spray towards a target tissue area to be treated, including an optical fiber duct, a water duct and an air duct, and an apparatus including a laser and a controller for water and air flow.

21 Claims, 26 Drawing Sheets

DENTAL SYSTEM FOR TREATMENT OF PERIODONTAL POCKETS LASER LIGHT

This application is the national phase under 35 U.S.C. §371 of PCT International Application No. PCT/DK99/00057 which has an International filing date of Feb. 8, 1999, which designated the United States of America.

FIELD OF THE INVENTION

The present invention relates to a dental system for treatment of periodontal pockets using laser light and having a handpiece with an optical fibre for directing laser light towards a target tissue area to be treated.

BACKGROUND OF THE INVENTION

It is known to utilise laser light for treatment of periodontal pockets.

During treatment laser light heats plaque by illumination thereby destroying living cells in the plaque so that a subgingival infection is stopped by laser treatment.

Lasers that operate at a wavelength that is moderately absorbed in water are used for this treatment. When the laser power density (W/mm2) at illuminated cells is sufficient, cellular water is heated by energy absorption causing a temperature rise in the cell that destroy heated cells.

During treatment, it is essential not to heat or damage surrounding tissue. Residual heat may affect the nerve of the tooth causing pain to the patient and/or may cause tissue to char and become necrotic. Thus, it is desirable to minimise transmission of conducted heat to underlying and surrounding tissue.

It is therefore desired to accurately control the amount of light energy transferred to plaque, calculus, tissue to be incised, etc, to be treated. The amount of energy must be sufficient for effectively treating matter, such as plaque, calculus, tissue, and, simultaneously, the amount of residual energy heating surrounding tissue must be too low to heat the tissue.

SUMMARY OF THE INVENTION

It is an object of the present invention to provide a denial system for treatment of periodontal pockets using laser light for laser surgery, such as laser gingivectomy, periodontal pocket curettage, etc, without heating surrounding tissue.

According to a first aspect of the invention, the above-mentioned and other objects are fulfilled by a dental system for treatment of periodontal pockets using laser light, comprising a handpiece for directing laser light and a coolant spray towards a target area to be treated. The handpiece comprises a housing with an input end and an output end and holds an optical fibre duct for receiving and holding an optical fibre and extending within the housing from the input end to the output end. During operation of the system, an optical fibre with a fibre output end for emission of the laser light is positioned in the optical fibre duct. Further, the optical fibre duct may hold a seal that is adapted to receive and hold the optical fibre in water tight engagement with the optical fibre duct. The housing also has an air duct for transmission of compressed air and extending within the housing from the input end to the output end and a water duct for transmission of water and extending within the housing from the input end The water duct leads into the optical fibre duct within the housing between the output end and the seal so that water flowing through the water duct leaves the housing at the output end through the optical fibre duct. The treating laser light to be emitted from the fibre output end is supplied by a laser in an apparatus that is connected to the fibre so that light from the laser is coupled into the fibre.

When treating laser light is emitted from the fibre output end, a spray coolant of mixed air and water is simultaneously emitted from the output end of the handpiece housing providing cooling of tissue surrounding the treated area illuminated by the laser light. Thus, the apparatus further comprises a water control member that is adapted to be interconnected between a water supply and the water duct and to control the amount of water flowing into the water duct, and an air control member that is adapted to be interconnected between a supply of compressed air and the air duct and to control the amount of compressed air flowing into the air duct.

The apparatus also has a controller for controlling the operation of the system and being connected to the water control member and the air control member and being adapted to set the amount of water flowing into the water duct in the range from 5 ml/min to 50 ml/min, preferably from 10 ml/min to 30 ml/min, and more preferred to approximately 20 ml/min.

Further the controller is adapted to set the pressure of compressed air flowing into the air duct so that a coolant spray of mixed air and water is formed. This may be done by provision of a user interface that is connected to the controller and that is utilised by an operator of the system to enter parameter values of the system to be set by the controller. The operator may in this way increase the pressure of compressed air until formation of the spray of mixed air and water is visually detected.

The amount of water forming the water spray is selected so that the amount is sufficient to effectively cool surrounding tissue not to be treated by the laser light while being less than an amount that would absorb so much laser light that treatment would be inhibited.

According to an important aspect of the present invention, the wavelength and the power level of the laser light are selected so that only matter that abuts the fibre output end is heated when illuminated by the laser light. Thus, there is no risk of harming tissue that is accidentally illuminated by laser light emitted from the fibre output end as the energy density in the emitted laser light decreases rapidly with distance from the fibre output end.

According to another important aspect of the present invention, efficient cooling of tissue surrounding target area being treated by the laser light is provided by directing a coolant spray of air and water towards the surroundings of the fibre output end. As the water leaves the housing through the fibre duct and at least some of the water continues to flow along the surface of the fibre, accurate directing of the air and water spray along a longitudinal axis of the fibre is provided. The amount and composition of the air and water spray and the amount of light energy supplied to the treatment area are selected so that efficient cooling of the surroundings of the treatment area is provided thereby effectively preventing conduction of heat from the treatment area while simultaneously raising the temperature of matter abutting the fibre output end sufficiently to destroy and preferably remove the matter.

Light of 1 $\mu$m wavelengths are moderately absorbed in water and the extinction length in soft tissue is about 1 to 3 mm. However, colour and structure of tissue have a great influence on absorption of light in this wavelength range and pigmented tissue absorbs light in this wavelength range efficiently. The light is for example absorbed in blood causing photocoagulation of blood and this effect is advantageously utilised during treatments with the present system.

Typically, the treatment is initiated when the fibre output end accumulates dark particles that is heated through light absorption. Plasma, a super-heated gas, may form on the surface abutting the fibre output end. Plasma absorbs the light and conducts heat to the matter to be treated, such as gingival tissue, plaque, calculus, etc. Plaque and tissue to be treated typically evaporates and calculus becomes brittle during treatment.

It should be recognised that many parameters of the treating light determine the effect of the treatment. Such parameters comprise the laser wavelength, laser power, laser waveform, tissue optical properties, tissue thermal properties, way of cooling, etc. The number of possible combinations of these parameters is infinite, many of which would result in inefficient treatment and/or unacceptable damage to tissue that should not be treated. Thus, the present invention is based on intensive research and clinical tests in the field of treatment of periodontal pockets using laser light.

As will be described in more detail below, this intensive research has revealed that it is possible to effectively treat periodontal pockets without damaging healthy tissue with a system according to the present invention.

The combination of average power in the emitted light and the repetition rate of emitted light pulses has to be set in a power range and a frequency range, respectively, wherein the above-mentioned thermal effects occur without a risk of damaging healthy tissue. It has been found that treatment with repetition frequencies below 50 Hz has resulted in unsatisfactory clinical results and that repetition frequencies below 70 Hz can be safely utilised without heating surrounding tissue at average power levels ranging from 1 to 10 W. Preferably the average power ranges from 3 W to 8 W. For pocket curettage it is preferred to set the average power ranging from 4 W to 6 W, and most preferred the average power is approximately 5 W and for laser surgery it is preferred to set the average power ranging from 5 W to 8 W, and more preferred from 6 W to 7 W.

The repetition frequency preferably ranges from 50 Hz to 70 Hz, more preferred from 55 Hz to 65 Hz, and still more preferred the repetition frequency is approximately 60 Hz.

Simultaneously, the duration of the light pulses must be within the range wherein sufficient energy is delivered to effectively heat matter to be treated without the average power attaining unsafe levels. According to the present invention it is preferred that the duration of the light pulses ranges from 150 $\mu$s to 500 $\mu$s, preferably from 200 $\mu$s to 300 $\mu$s, more preferred that the duration is approximately 250 $\mu$s.

It is an important advantage of the present invention that the emitted laser light causes photocoagulation of blood so that possible bleeding of treated tissue is quickly stopped.

The laser may be any laser capable of emitting light of suitable wavelength and with sufficient power for illuminated matter to be treated, such as Nd YAG lasers, NCG lasers, diode lasers, etc.

A Nd YAG laser emits light at a wavelength of 1.064 $\mu$m. The Nd YAG laser is particularly well suited as a light source in a dental system for treatment of periodontal pockets as water has a moderate energy absorbance at 1.064 $\mu$m so that heating of matter abutting the fibre output end is provided while simultaneously allowing water in the coolant spray impeding on surrounding matter to effectively cool the surroundings of the matter being treated. Further, the Nd YAG laser is capable of reliably delivering the required laser power.

The optical fibre of the handpiece according to the present invention may be any fibre, such as an optical fibre made of pure silica, etc, that is suitable for transmission of light emitted from the laser and that is made of a material that allows repeated bending of the fibre so that an operator can freely manipulate the handpiece, e.g., in order to insert the fibre output end into a periodontal pocket of a patient. It is preferred that the outer diameter of the fibre ranges from 300 $\mu$m to 600 $\mu$m, and presently it is preferred to use fibres with an outer diameter of approximately 400 $\mu$m or approximately 600 $\mu$m.

For an operator of the system to be able to treat a suitable area during a suitable time period, it is presently preferred that the laser is adapted to emit light for a period ranging from 10 s to 1 minutes upon user activation, and more preferred for a period ranging from 20 s to 50 s upon user activation, and even more preferred for a period of approximately 30 s upon user activation.

The user interface may comprise a foot pedal for activation of the system so that light is emitted from the fibre output end upon activation of the foot pedal.

The controller may comprise at least one timer for accumulation of the time during which light has been emitted by the system. A timer value may be displayed to the operator of the system on the user interface. The timer value may be utilised by the operator of the system for calculation of cost of a treatment.

A timer value may be read by a service technician during maintenance of the system, e.g., in order to decide whether preventive service tasks have to be performed or not.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

In the following, a preferred embodiment of a dental system for treatment of periodontal pockets using laser light will be described with reference to the drawings, wherein.

DETAILED DESCRIPTION OF THE DRAWINGS

Figure 1:
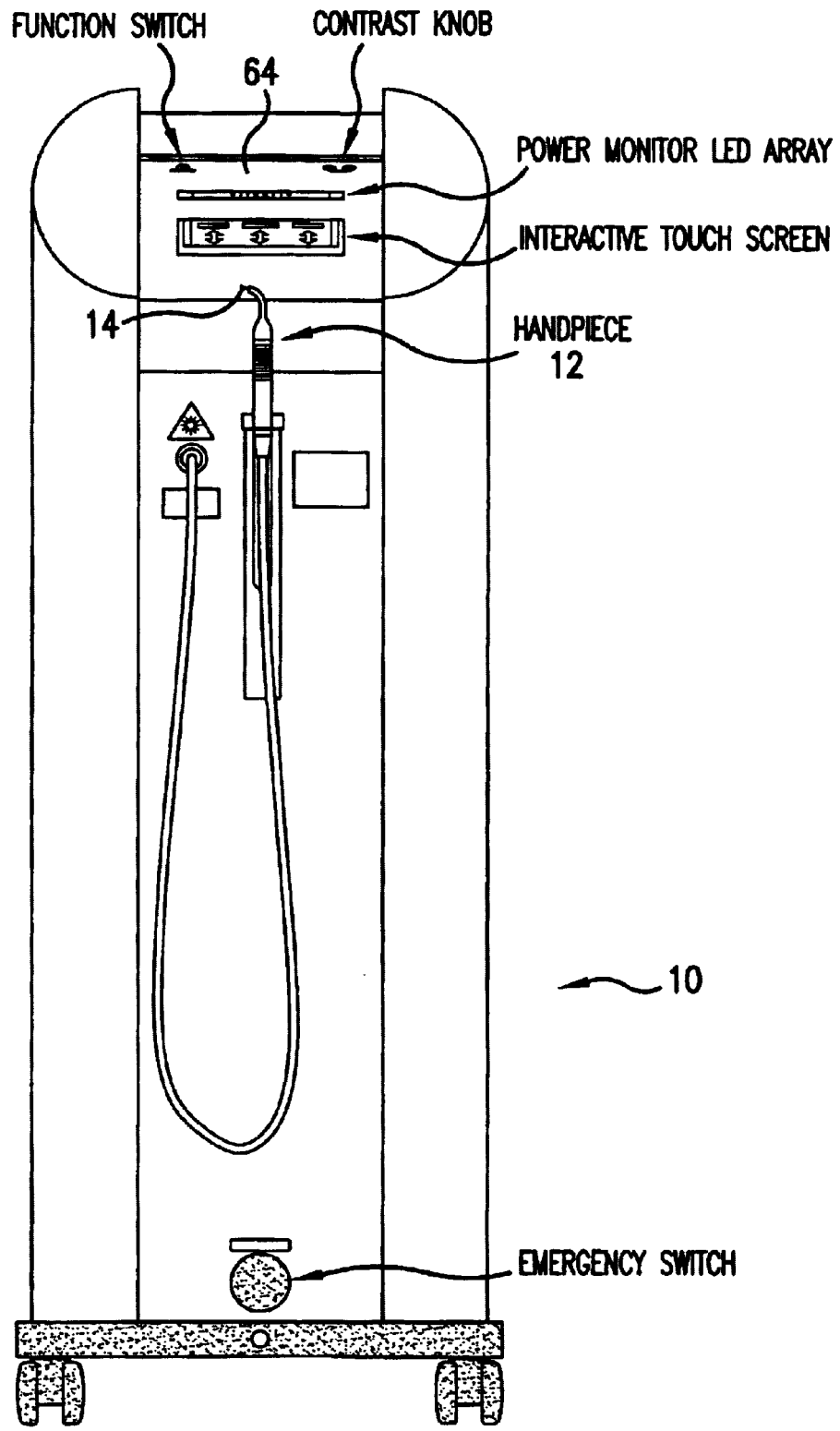
FIG. 1 is a front view of a system according to the invention.

Referring to FIGS. 1–5, the system 10 according to the present invention comprises a handpiece 12 with an fibre output end 14 for treatment of e.g. periodontal pockets. Light to be emitted from the fibre output end 14 is supplied by a laser 16 that is coupled to the fibre with a fibre coupler 18. The laser 16 is pumped by a flash lamp that is ionised by a voltage pulse generated by a simmer module 22. When the flash lamp 20 gas is ionised the simmer module 22 maintains a small simmer current. The simmer module 22 provides about 1000 $V_{DC}$ to the flash lamp 20. The simmer module 22 then generates 1 ms pulses of 200–300 $V_{DC}$ at 27 Hz to a trigger transformer until the flash lamp 20 gas ionises. A voltage sensor circuitry inside the simmer module 22 detects the gas ionisation and stops the simmer pulses. After the initiation the voltage drops to approximately 135 $V_{DC}$.

A high voltage power supply 34 generates a 400 $V_{DC}$ output supplied to the capacitors 24, 26.

Figure 15:
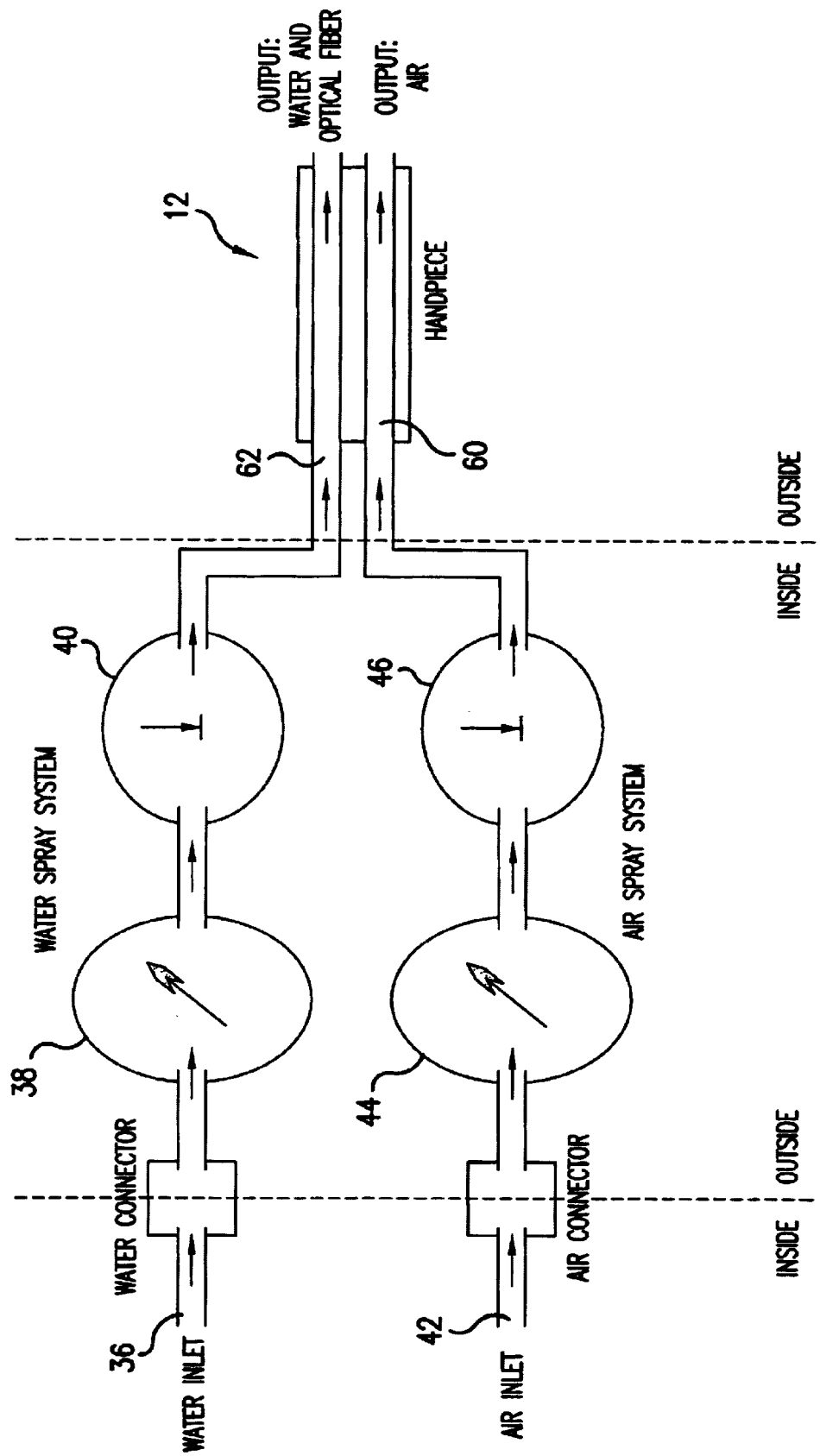
FIG. 15 shows schematically an air and water spray supply system of the system shown in FIG. 1.
Figure 16:
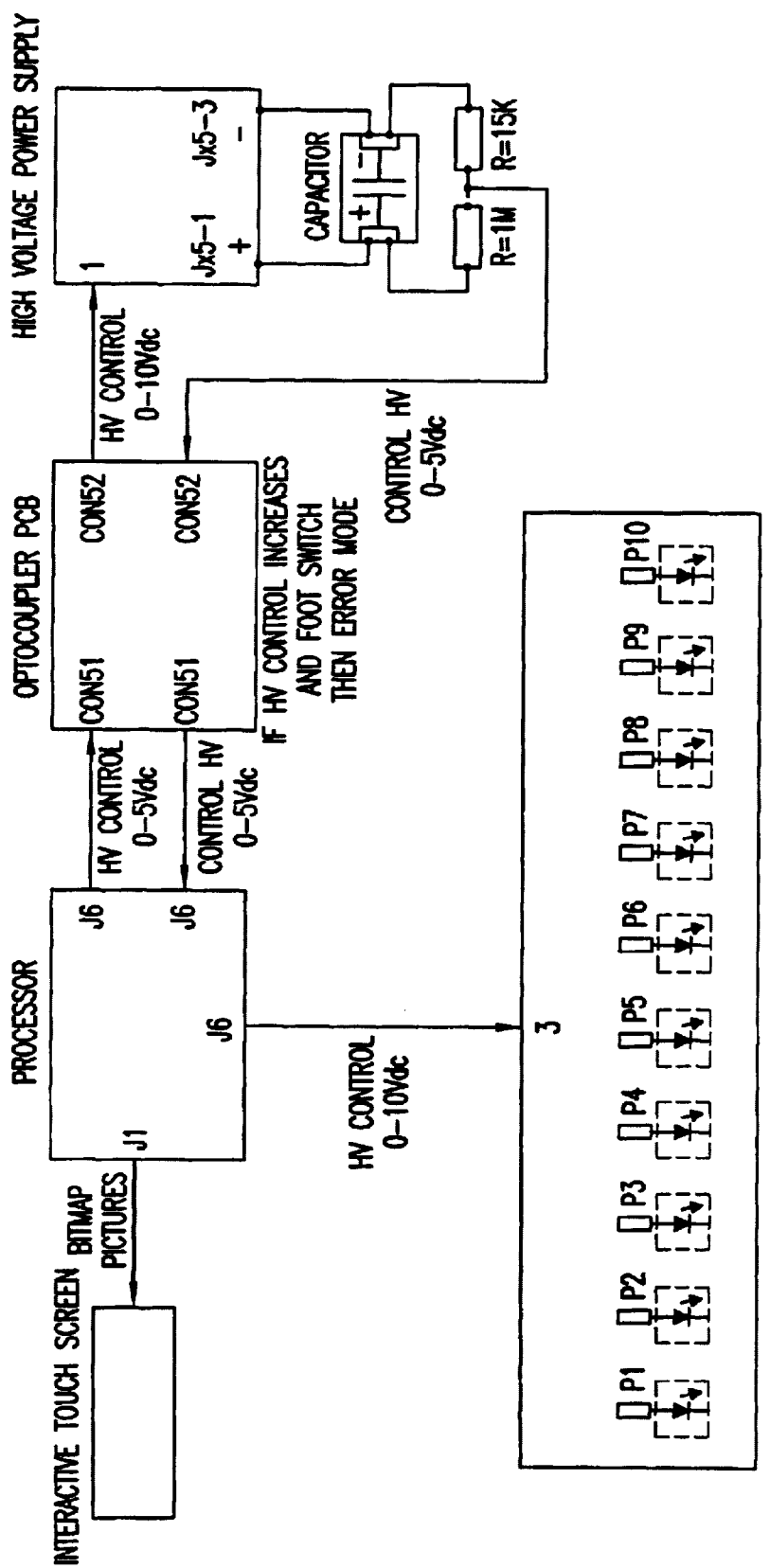
FIG. 16 is a circuit diagram of the laser output power control system of the system shown in FIG. 1.
Figure 17:
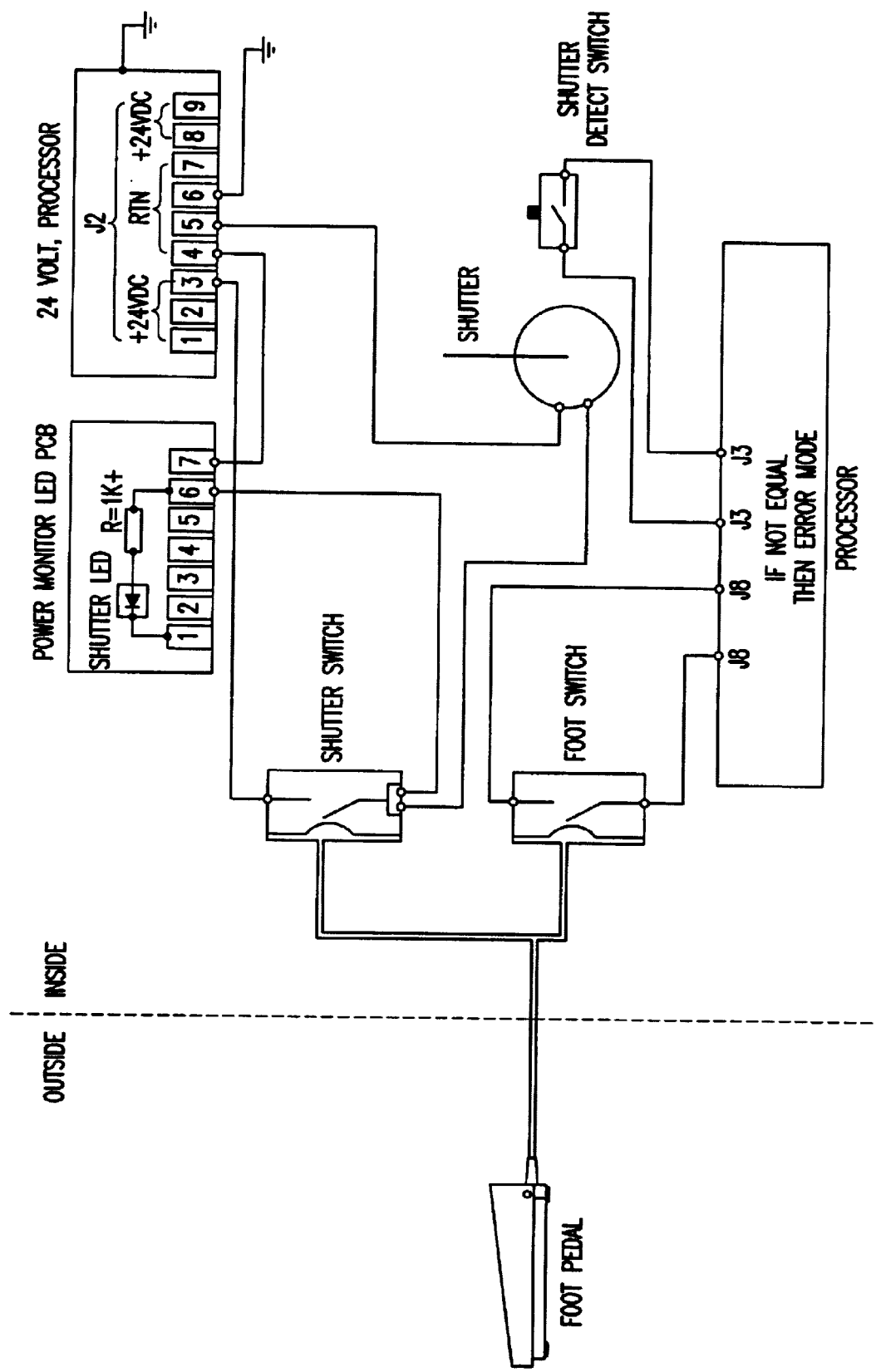
FIG. 17 is a circuit diagram of a shutter system of the system shown in FIG. 1.

As also shown in FIG. 15, water and air for the mixed air and water spray generated at the fibre output end 14 at the handpiece 12 is supplied from a water inlet 36. From the water inlet 36 water flows through a reduction valve 38 and thereafter through a linearly controlled solenoid valve 40 that controls the amount of water delivered to the handpiece 12. The valve 40 is controlled by the controller 32. Likewise, air flows from an air inlet 42 through a reduction valve 44 and thereafter through a linearly controlled solenoid valve 46 that controls the amount of air delivered to the handpiece 12. The valve 46 is also controlled by the controller 32.

High voltage for driving the flash lamp 20 is supplied from two capacitors 24, 26. The high voltage is controlled by an IGBT 28 which again is controlled by an IGBT drive circuit 30. A trigger signal for the IGBT drive circuit 30 is supplied by a controller 32.

Figure 6:
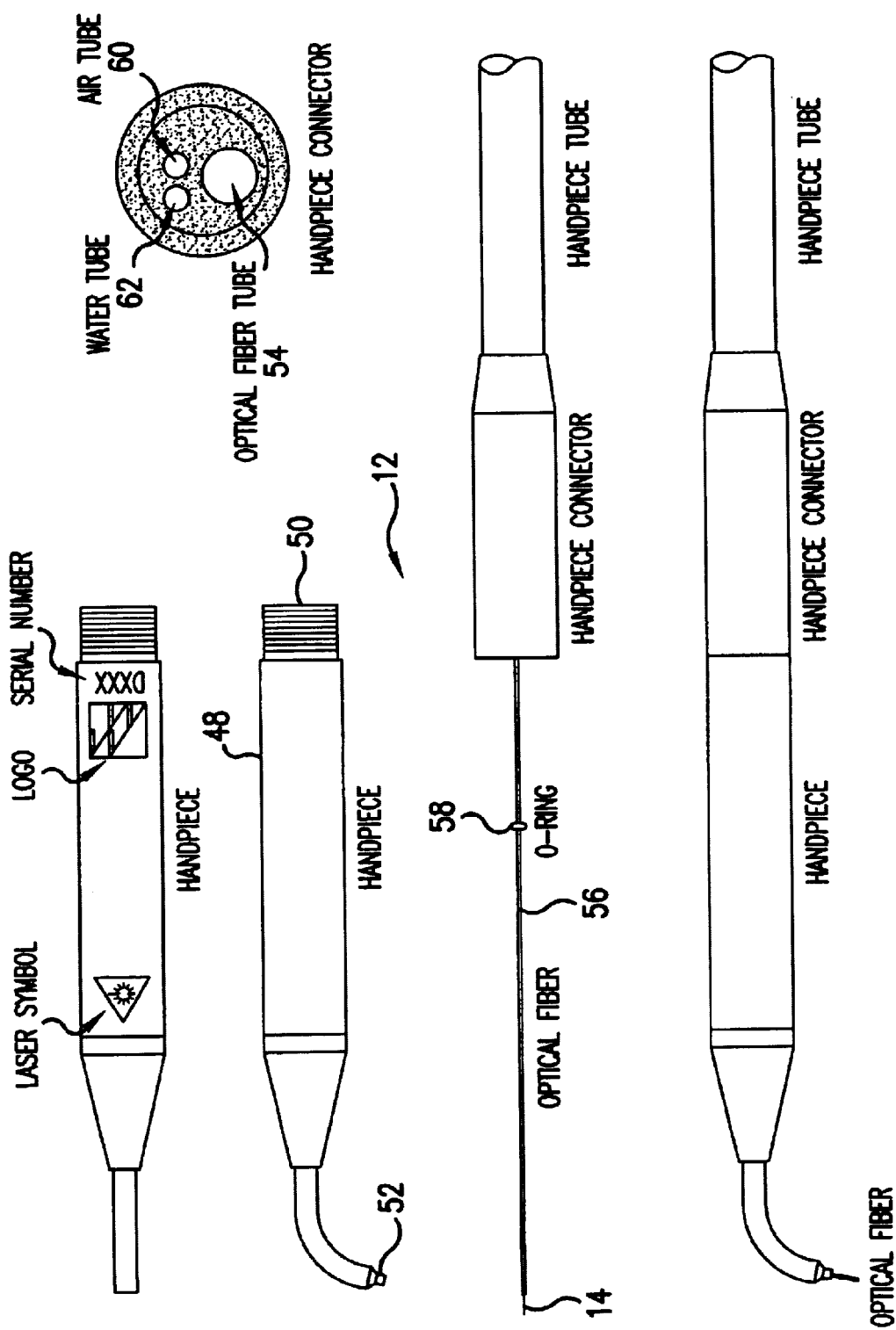
FIG. 6 shows schematically the construction of a handpiece according to the invention.
Figure 7:
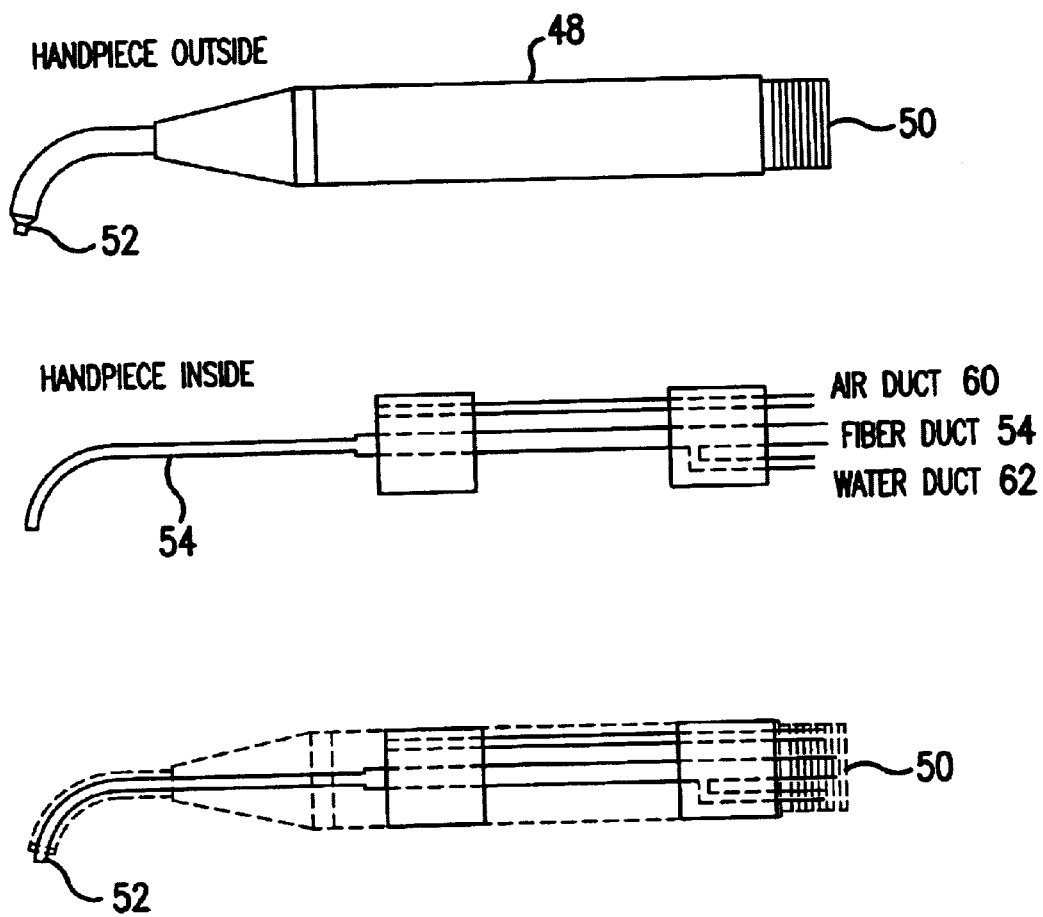
FIG. 7 shows the supply ducts in the handpiece shown in FIG. 6.

FIGS. 6 and 7 shows schematically the construction of a handpiece according to the invention for directing laser light and a coolant spray towards a target area to be treated. The handpiece 12 comprises a housing 48 with an input end 50 and an output end 52 and holds an optical fibre duct 54 for receiving and holding an optical fibre 56 and extending within the housing 48 from the input end 50 to the output end 52. During operation of the system, an optical fibre 56 with a fibre output end 14 for emission of the laser light is positioned in the optical fibre duct 54. Further, the optical fibre duct 54 holds a seal 58 that is adapted to receive and hold the optical fibre 56 in water tight engagement with the optical fibre duct 54. The housing 48 also has an air duct 60 for transmission of compressed air and extending within the housing 48 from the input end 50 to the output end 52 and a water duct 62 for transmission of water and extending within the housing 48 from the input end 50. The water duct 62 leads into the optical fibre duct 54 within the housing 48 between the output end 52 and the seal 58 so that water flowing through the water duct 62 leaves the housing 48 at the output end 52 through the optical fibre duct 54.

Figure 8:
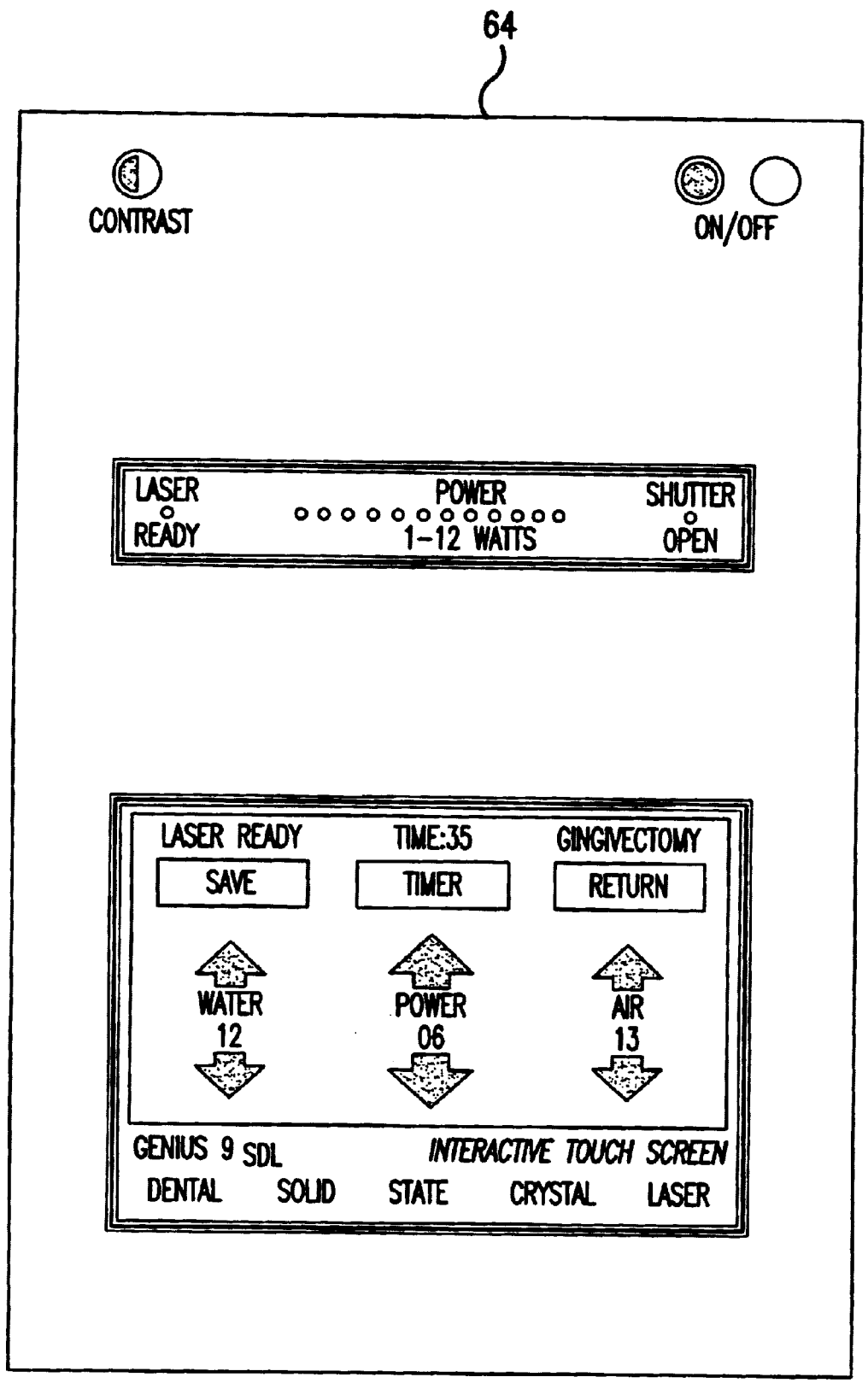
FIG. 8 shows a front panel of the user interface of the system shown in FIG. 1

FIG. 1 and FIG. 8 show a front panel 64 of the user interface of the system shown in FIG. 1.

EXAMPLES

Figure 9:
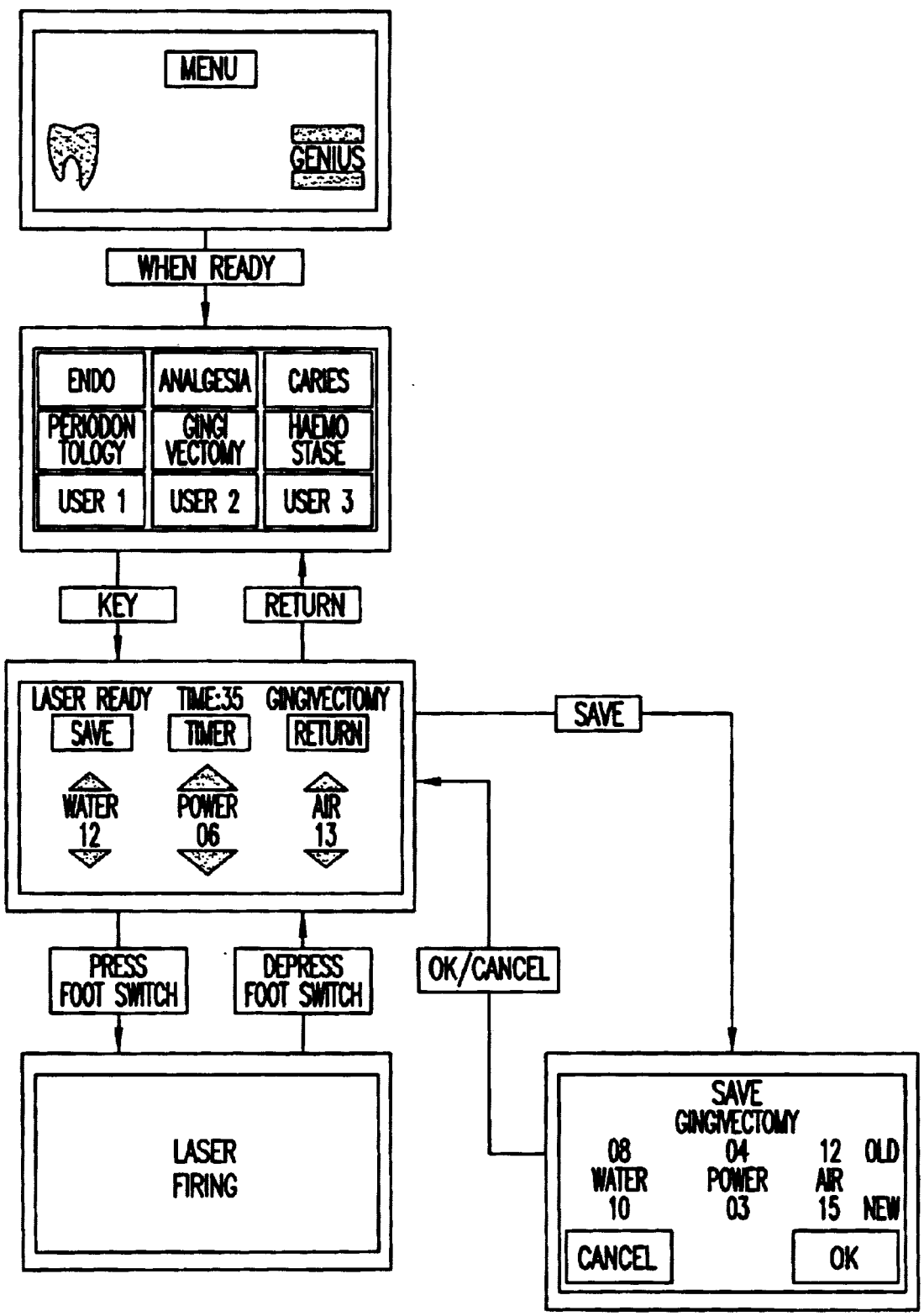
FIG. 9 is a flow diagram of the operation of the system shown in FIG. 1.
Figure 10:
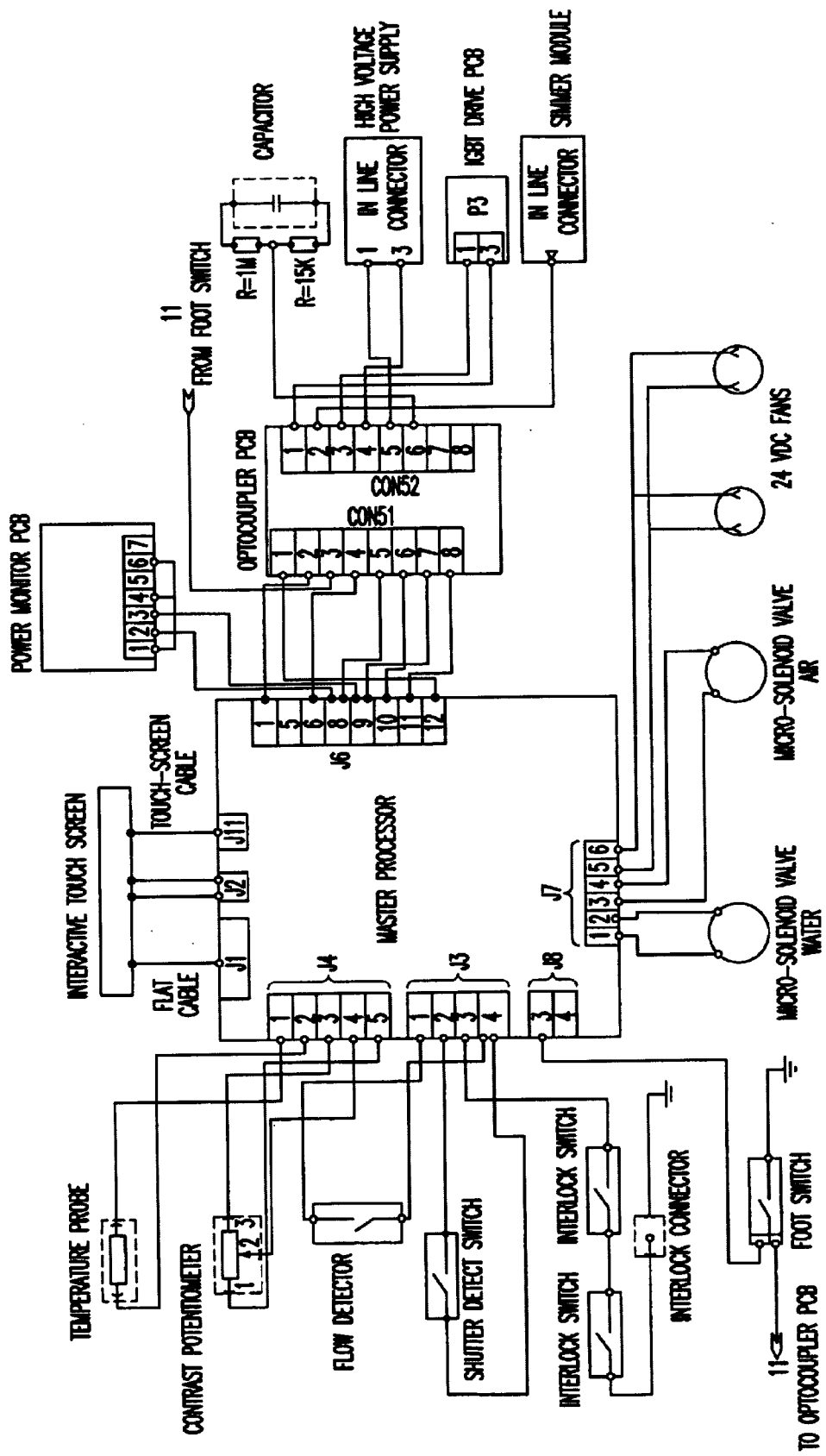
FIG. 10 is a circuit diagram of the control signals of the system shown in FIG. 1.
Figure 11:
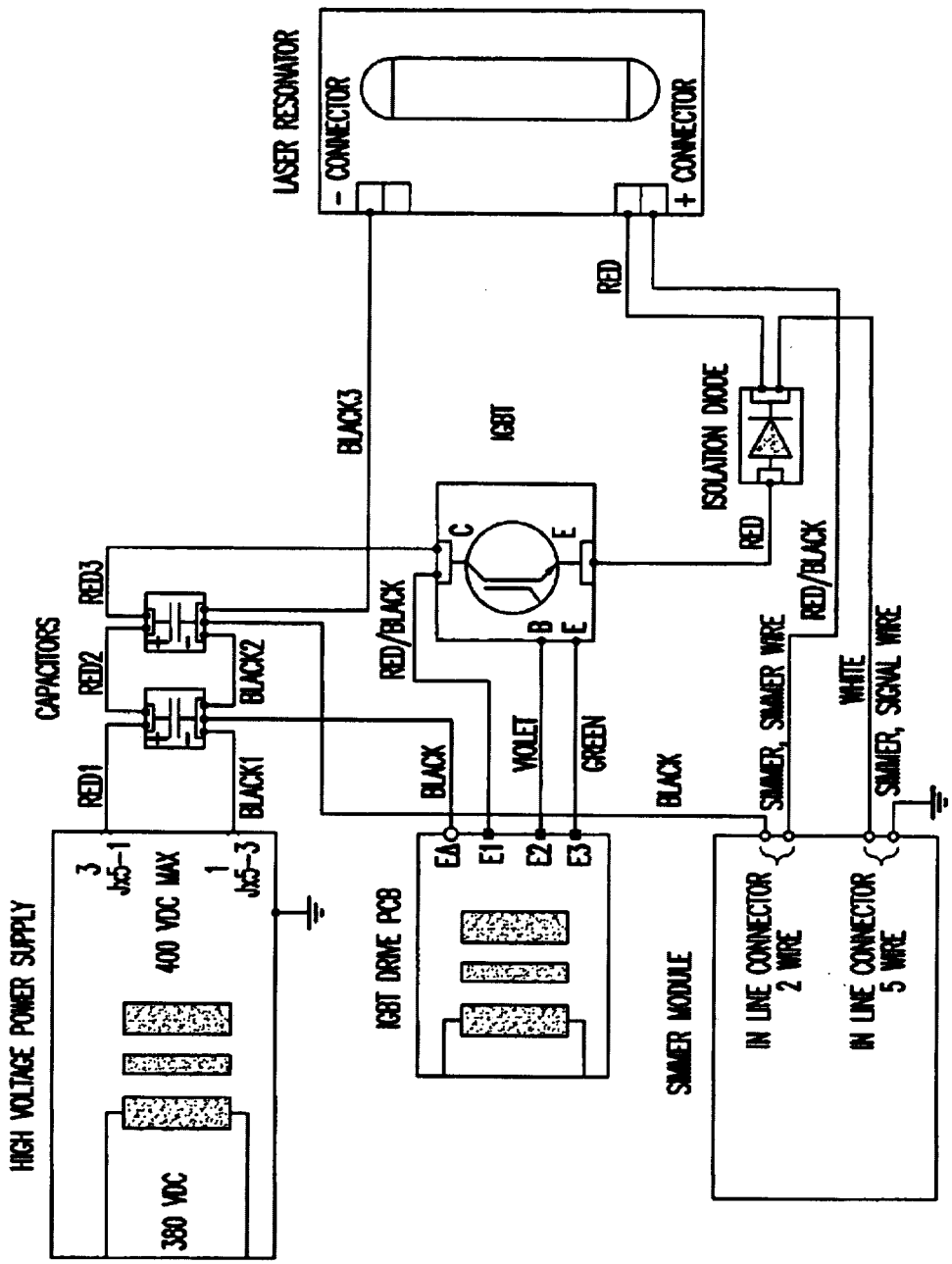
FIG. 11 is a circuit diagram of the high voltage supply interconnections of the system shown in FIG. 1.
Figure 12:
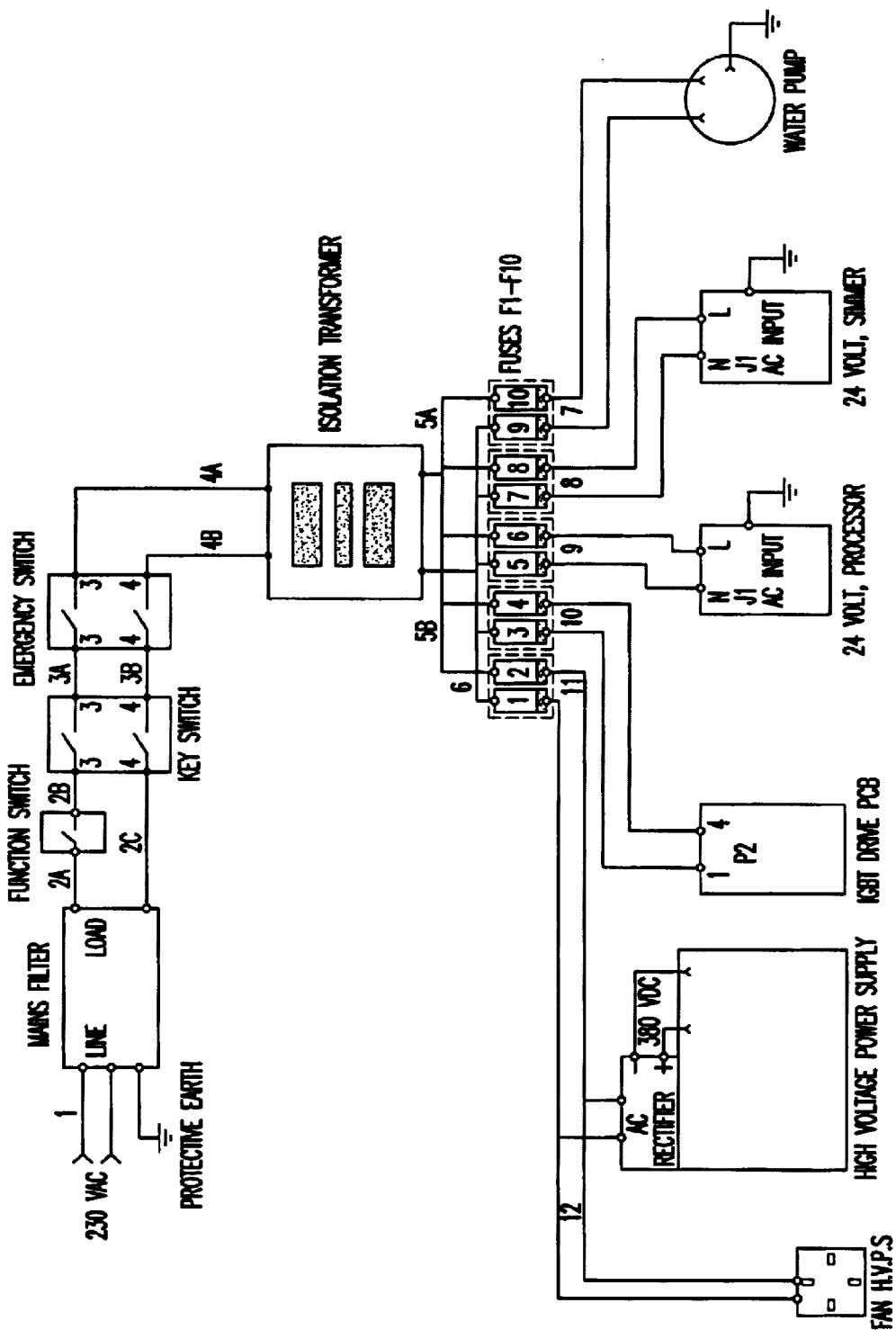
FIG. 12 is a circuit diagram of the AC line interconnections of the system shown in FIG. 1.
Figure 13:
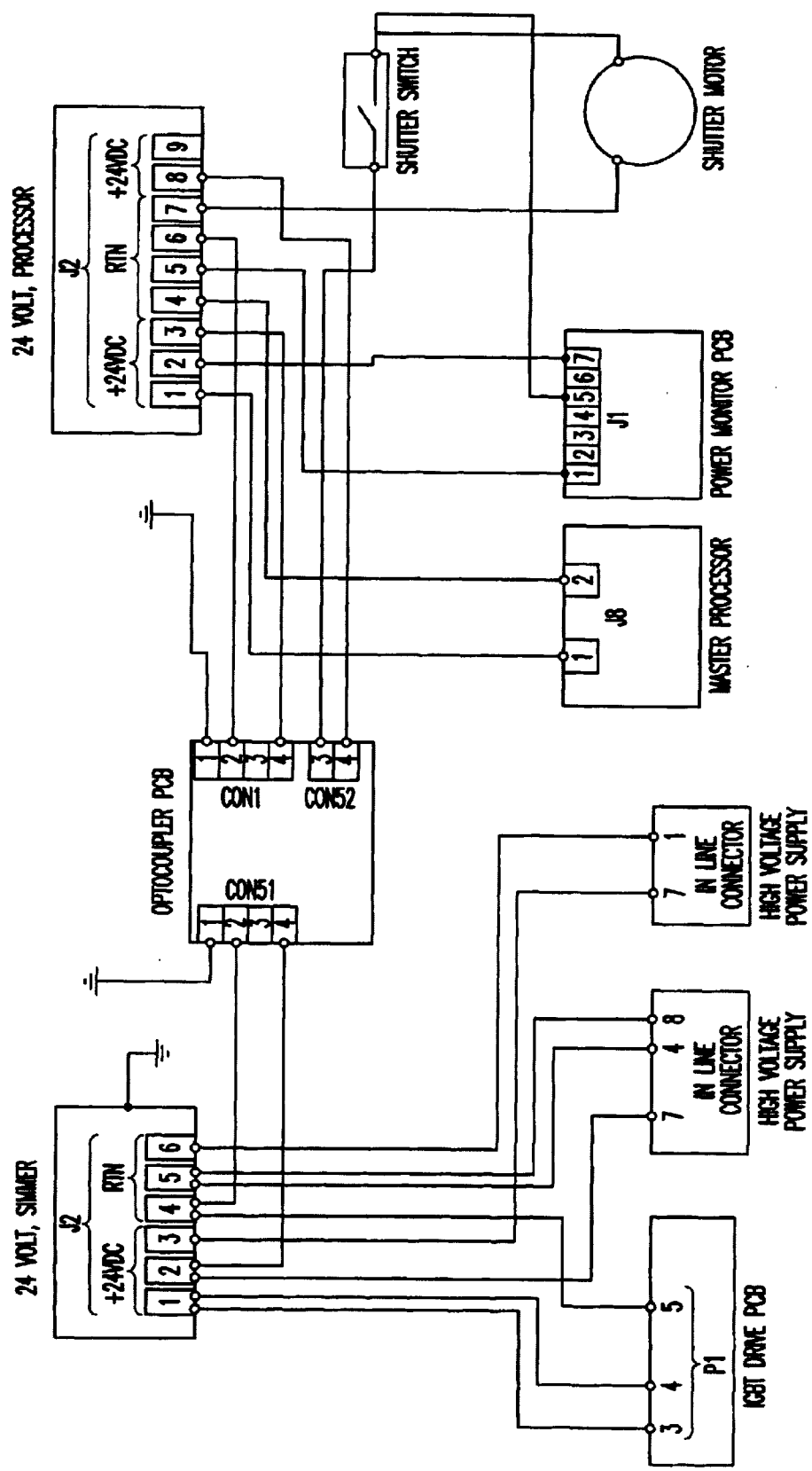
FIG. 13 is a circuit diagram of the 24 $V_{DC}$ interconnections of the system shown in FIG. 1.
Figure 14:
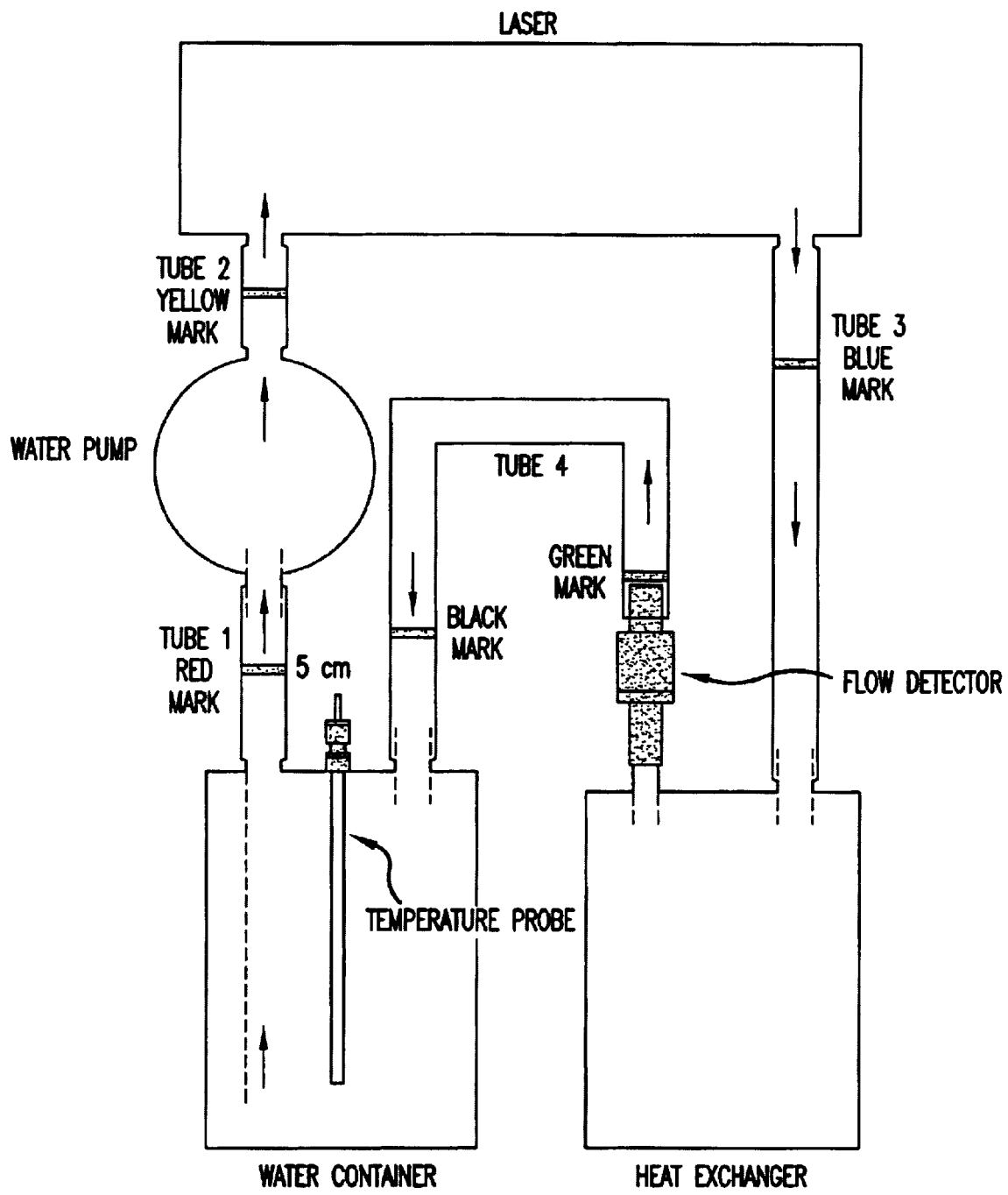
FIG. 14 shows schematically a cooling system of the system shown in FIG. 1.

When the system is used for dental treatments, the "periodontology" button (FIG. 9) is activated and the laser parameter are adjusted as described below. The timer may be used for controlling total time of treatment.

Figure 18A:
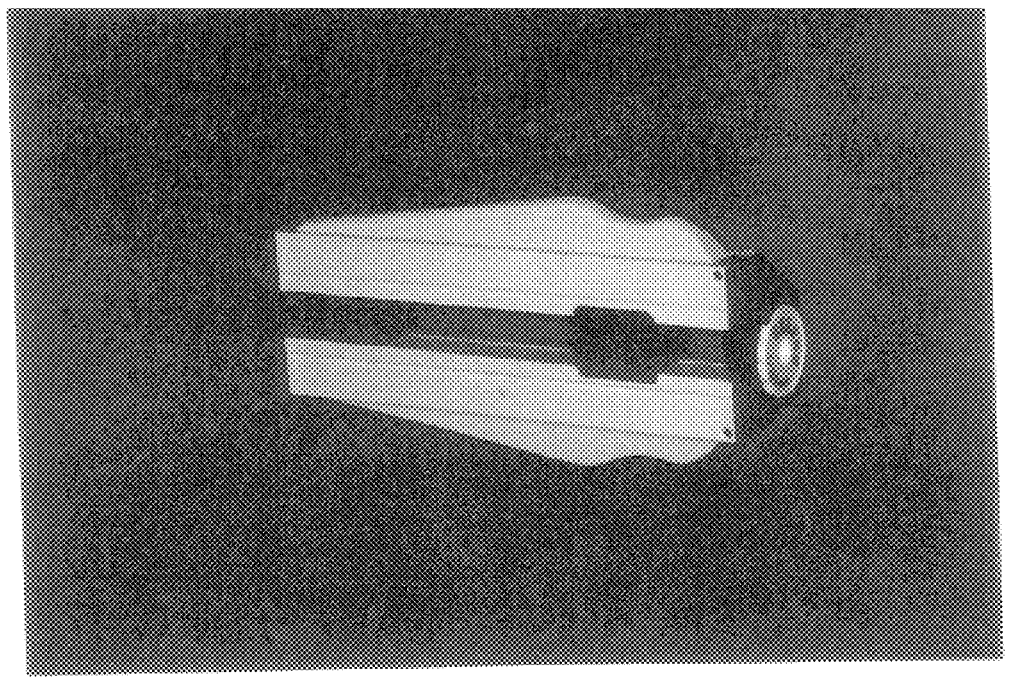
FIG. 18 shows a fibre cutter.
Figure 18B:
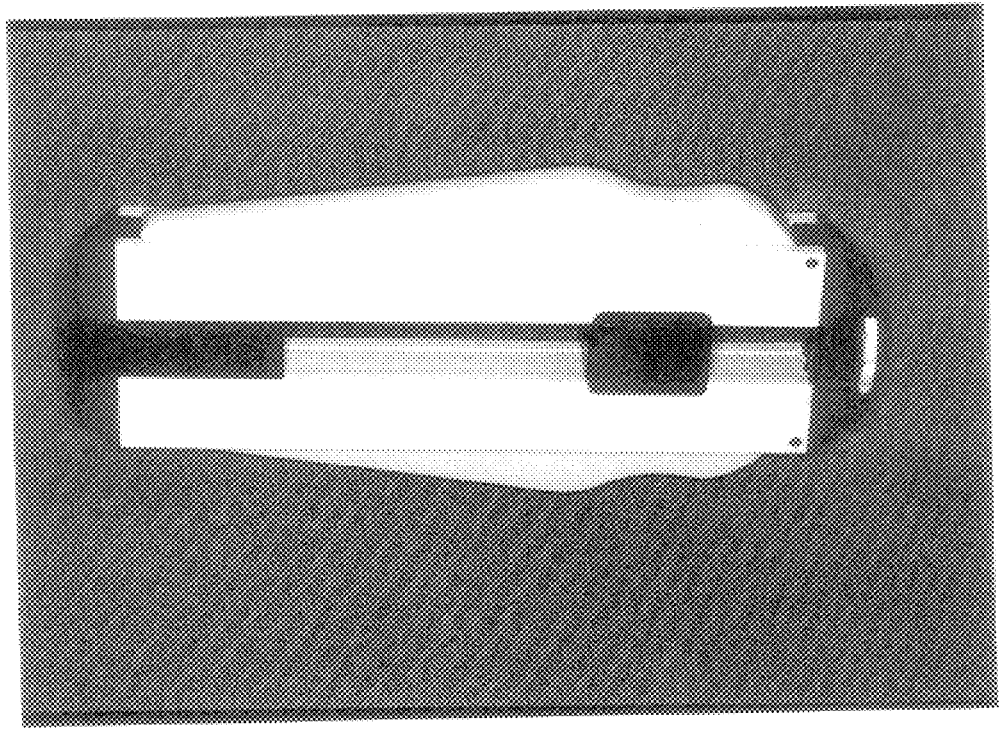
Figure 19:
FIG. 19 shows insertion of an optic fibre into the cutter shown in FIG. 18.
Figure 20:
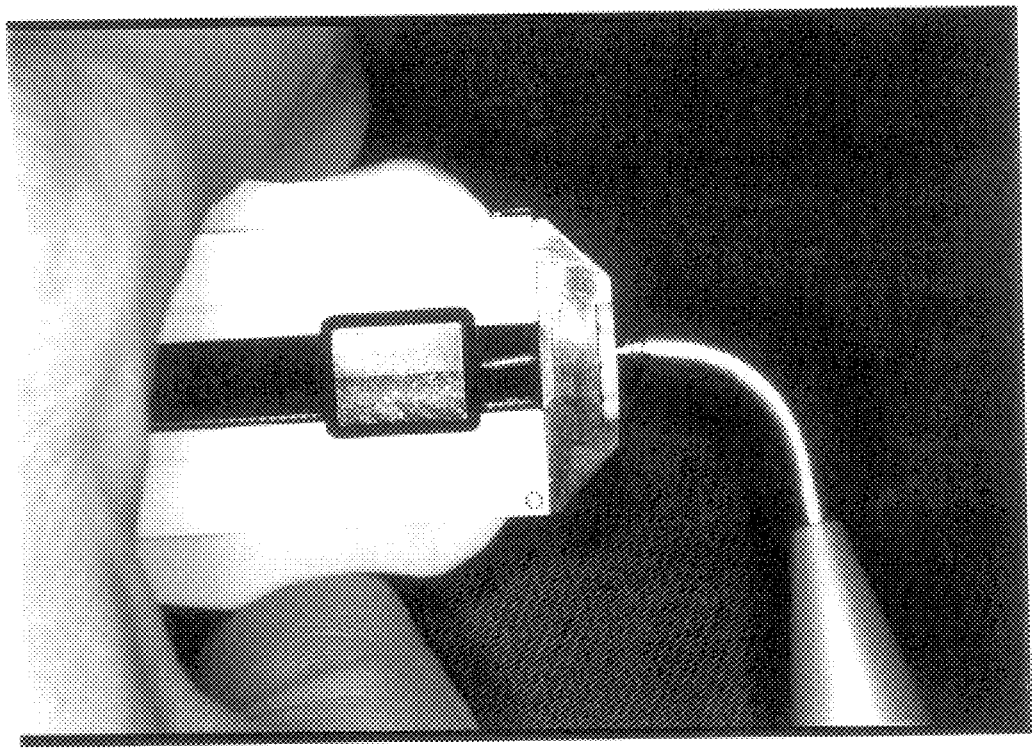
FIG. 20 shows stripping off a protective layer around an optic fibre inserted into the cutter as shown in FIG. 19.
Figure 21:
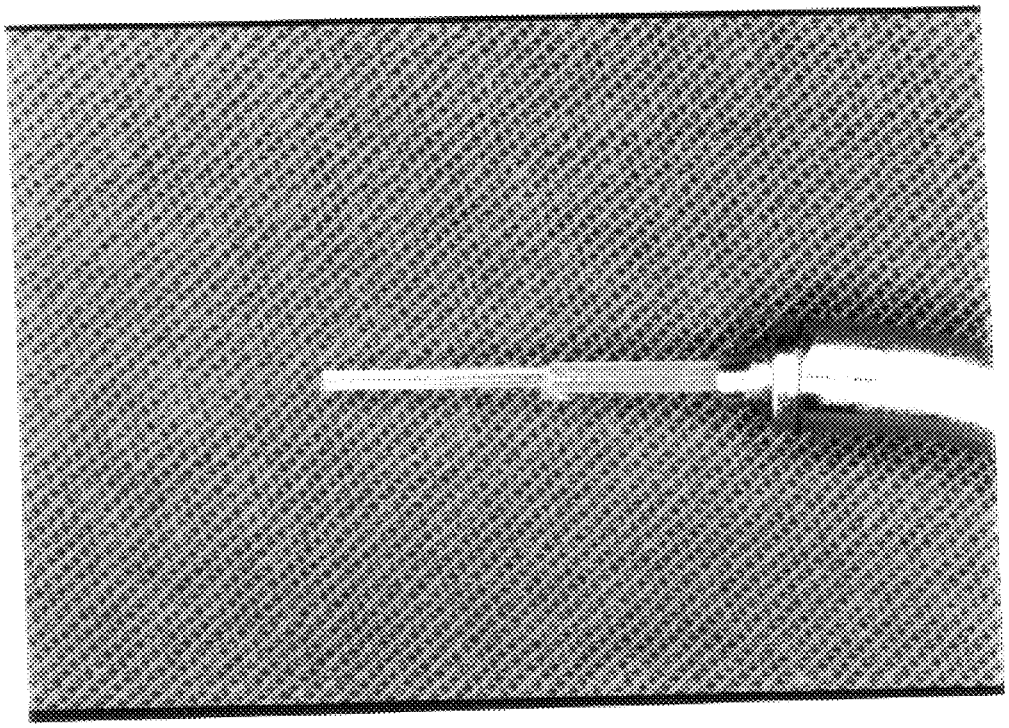
FIG. 21 shows a stripped fibre with a desired length of optic fibre exposed.
Figure 22:
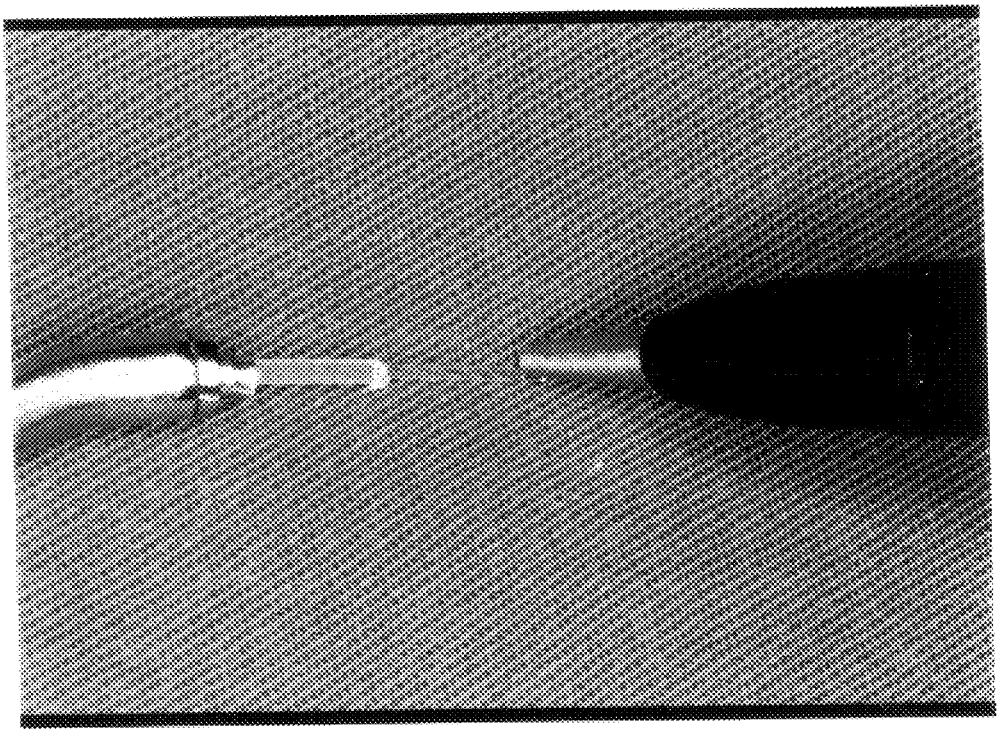
FIG. 22 illustrates cut off of a used piece of fibre with a diamond pen.

Further the length of the optical fibre is adjusted to correspond to the depth of the pocket by means of a fibre cutter as shown in FIGS. 18a and 18b. The sliding device shown in FIG. 19 is adjusted to the desired length and the fibre covered with a protective layer is inserted into the cutter. The protective layer is stripped off as shown in FIG. 20 by pressing the edges of the cutter while retracting the fibre from the cutter. This results in the exposure of the desired length of the optical fibre as shown in FIG. 21. After end of treatment, the handpiece is disconnected from the system and sterilised in an autoclave. Before start of a new treatment, the autoclaved handpiece is connected to the system and a piece of optical fibre is cut off with a diamond pen as shown in FIG. 22. These measures prevent contamination of the handpiece and the fibre and transfer of e.g. bacteria from one patient to another.

Example 1

Pocket Curettage with Laser

Applications.

Treatment of periodontal pockets with PPD of 4–6 mm or deep pockets during the initial hygienic phase.

Laser Parameters

| Power: 5 W | Water: 4–7 | Air: 3–5 | Time: 30–120 seconds per site |
| --- | --- | --- | --- |

Local anesthesia is not required.

Technique.

Figure 23:
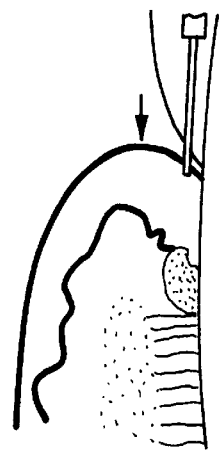
FIG. 23 illustrates positioning of a fibre tip in contact with gingiva at the entrance of a pocket.
Figure 24:
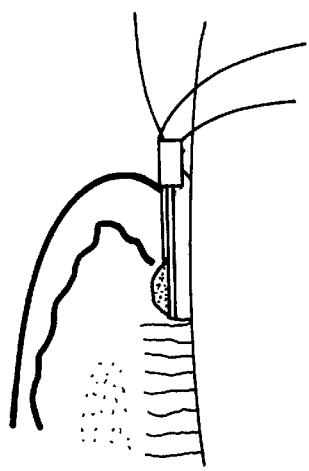
FIG. 24 illustrates the fibre tip having reached the bottom of the pocket.
Figure 25:
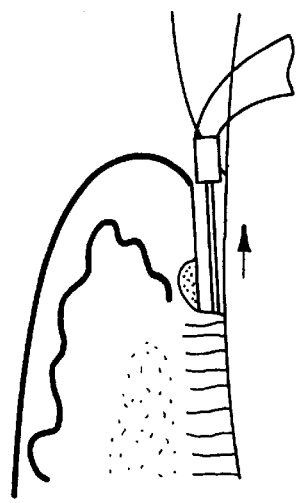
FIG. 25 illustrates withdrawal of the fibre from the pocket.

Adjust the length of the optic fibre according to the depth of the pocket scheduled for the treatment. During pocket curettage the laser fibre is always hold parallel to the root of the tooth. Activate the laser, and place the fibre tip in contact with gingiva at the entrance of the pocket (FIG. 23). Then, slowly insert the fibre into the pocket by moving it in the buccolingual direction at proximal sites, while in the mesiodistal direction at buccal or lingual sites. Placement of the fibre into the pocket is usually painless. The fibre, held in contact with the soft tissues, is then slowly moved apically until the bottom of the pocket is reached. This procedure results in gradual vaporizing of the pocket epithelium, subgingival plaque and some granulation tissues (FIG. 24). The laser fibre, held in contact with the root surface, is then moved coronally and withdrawn from the pocket in order to vaporize microbial debris on the root surface (FIG. 25). Remaining mineralized deposits, if present, are easily detected with a non-activated fibre and removed with a curette. Usually, this procedure requires 30–120 seconds per site.

Example 2

Laser Surgery

Applications

Elimination of periodontal pockets with PPD>6 mm, gingival enlargement, furcation involvements. Prior to surgery, all patients have to complete the hygienic phase, which includes OH-instruction, removal of supra- and subgingival deposits.

Laser Parameters

All laser surgeries should be performed using the following parameters:

| Power: 6–7 W | Water: 4–7 | Air: 3–5 |
| --- | --- | --- |

Local anesthesia usually is not required.

Technique

Supra-alveolar periodontal pockets or gingival hyperplasias

Figure 26:
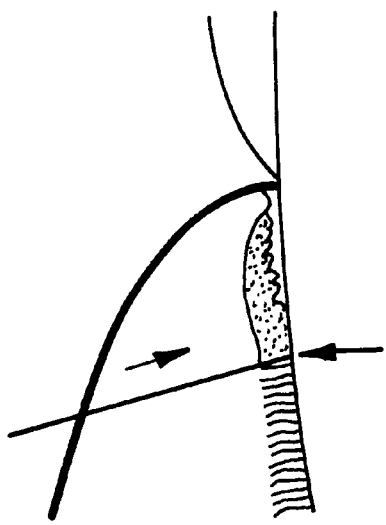
FIG. 26 illustrates a bevelled incision at the bottom of the pocket through the gingiva and abutting the tooth surface.
Figure 27:
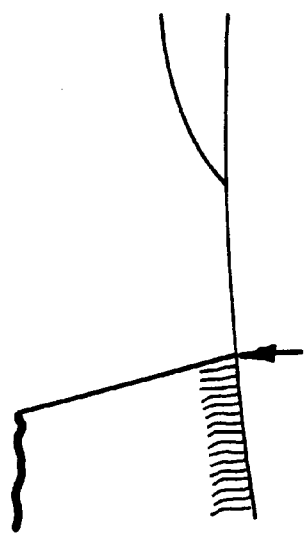
FIG. 27 illustrates the site shown in FIG. 26 after removal of excised tissue.

For treatment of these lesions laser gingivectomy is performed. Identify the depth and type of pocket around each tooth scheduled for the treatment. A beveled incision is made at the level of the bottom of the pocket through the gingiva onto contact with the tooth surface (FIG. 26). The excised tissue is removed with a curette or forceps (FIG. 27).

Figure 28:
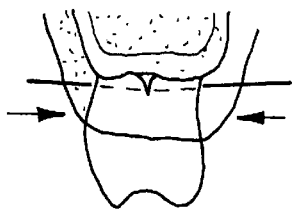
FIG. 28 illustrates bevelled incisions on the buccal and oral aspects at interproximal sites.
Figure 29:
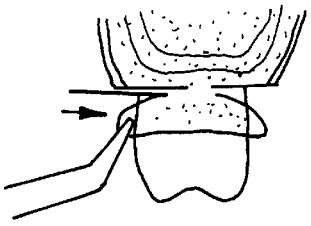
FIG. 29 illustrates separation with a fibre of dissected free tissue having been lifted with a curette or forceps.
Figure 30:
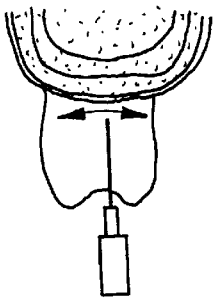
FIG. 30 illustrates treatment of exposed root surfaces with laser light for vaporising bacteria.

At interproximal sites, the beveled incisions are made on the buccal and oral aspects (FIG. 28). Then, the dissected free tissue is lifted with a curette or forceps and separated from the interdental periodontium with the laser (FIG. 29). The exposed root surfaces are then treated with the laser for vaporizing bacteria (FIG. 30) and scaled, if calculus is present.

Infrabony Defects

Figure 31:
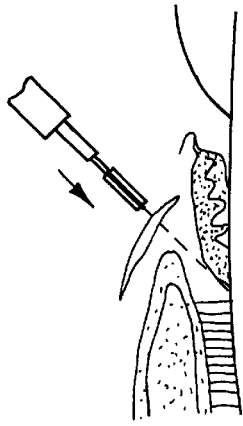
FIG. 31 illustrates a reverse bevel incision used for treatment of infrabony defects.
Figure 32:
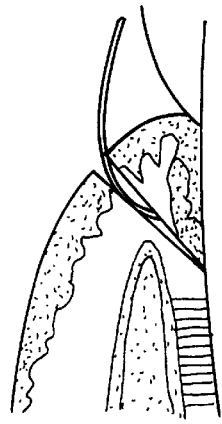
FIG. 32 illustrates removal with a curette of pocket epithelium after gradual deepening of the incision shown in FIG. 31.

In such defects, the bottom of the pocket is located below the bone level. Therefore, a "reverse bevel incision" is used for the treatment of such lesions. The fibre is angled at approximately 45 degrees to the long axis of the tooth (FIG. 31). The laser is activated and an initial incision is made. By gradually deepening the incision towards the bottom of the pocket, the pocket epithelium and the granulation tissue are dissected free and removed with a curette (FIG. 32). In case of post-surgical bleeding, move the fibre over the operated area for a few seconds to coagulate the blood vessels. The exposed root surfaces are then treated with the laser for vaporizing bacteria and scaled, if calculus is present.

Furcation-involved Teeth

For the treatment of degree II furcations, a gingivectomy is performed at the furcation area. Access to the furcation defect is obtained by means of horizontal incision with the laser fibre held horizontally and directed to the base of the pocket onto contact with the tooth surface. The dissected soft tissue flap is removed, and the remaining granulation tissue in the furcation defect is vaporized with the laser. The exposed root surfaces are then treated with the laser for vaporizing bacteria and scaled, if calculus is present.

For treatment of degree III furcations, a tunneling procedure is performed.

Figure 33:
FIG. 33 illustrates horizontal incisions directed towards the base of the pocket at the buccal and lingual sides of a tooth.
Figure 34:
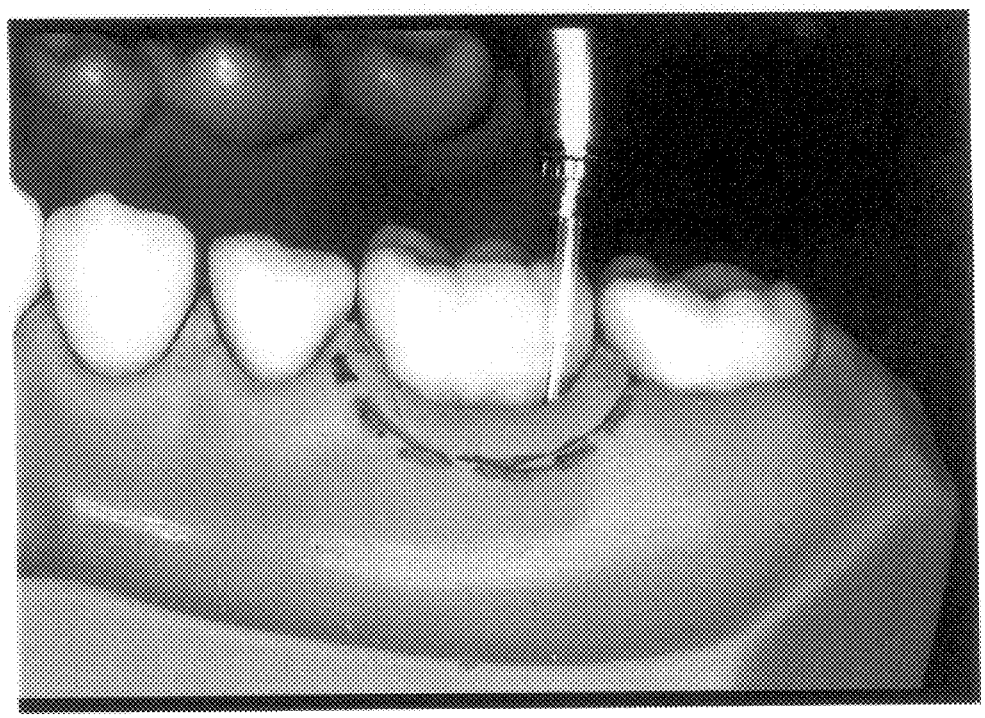
FIG. 34 illustrates vertical intracrevicular incisions produced at both sides of the tooth.
Figure 35:
FIG. 35 illustrates horizontal incision for excision of granulation tissue in the furcation.
Figure 36:
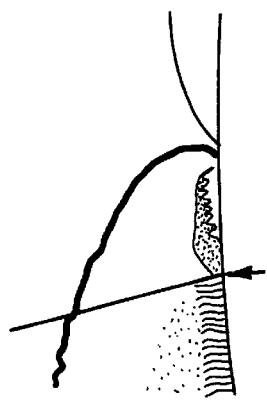
FIGS. 36–38 illustrate epithelization of a wound after laser surgery.
Figure 37:
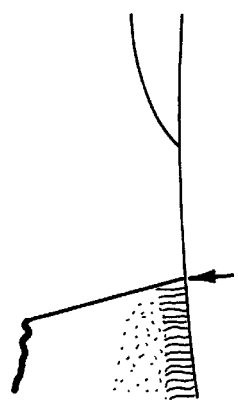
Figure 38:
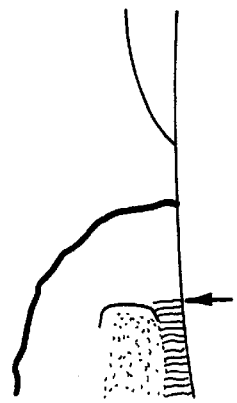

Horizontal incisions, directed towards the base of the pocket, are made at the buccal and lingual sides of the tooth (FIG. 33). Then, the vertical intracrevicular incisions are produced at both sides which allow the removal of the soft tissue flaps at the furcation entrance and facilitate the access to the furcation (FIG. 34). Then, the granulation tissue in the furcation is excised by means of a horizontal incision and removed with a curette or forceps (FIG. 35). The root surfaces are disinfected with the laser, and the remaining calculus, if present, is removed with a curette. Then, the patient is instructed in the use of interdental brushes in the opened furcation. In case of post-surgical bleeding, move the fibre over the operated area for a few seconds to coagulate the blood vessels.

Post-operative Care and Healing

During the laser surgery, a layer of connective tissue is preserved on the alveolar bone. Therefore, periodontal dressing is not applied after surgery. The operated area is rinsed with 0.2% chlorhexidine for a week. Thereafter, tooth brushing is reinstituted and a patient is instructed in the use of cleaning devices for self-performed plaque control. Epithelization of the wound is usually complete after 1–2 weeks with the establishment of a junctional epithelium adjacent to the root surface (FIG. 7). After laser surgery a healthy dentogingival unit is formed located at an apically displaced level in comparison with that at baseline.

Example 3

TREATMENT OF DENTINAL HYPERSENSITIVITY

The suggested hypotheses behind this finding is closing of the opened dentin tubules with a thin layer of silica during laser therapy. High temperature achieved at the tip of an optic fibre, held in contact with a root surface during laser firing, facilitates an even deposition of silica on the root surface, thus, resulting in decrease or elimination of tooth hypersensitivity.

Laser parameters

Treatment of hypersensitive teeth should be performed in two phases. At the beginning of the therapy, patients are extremely sensitive to water and air, therefore, the following parameters are used in the initial phase:

| Power: 2–3 W | Water: 1–2 | Air: 1–2 | Time: 15–25 seconds |
|---|---|---|---|

The laser fibre is always held parallel to the root surface.

This treatment results in the initial deposition of the silica layer over the dentinal tubules and decrease of hypersensitivity.

In the second phase the following parameters are used:

| Power: 4–5 W | Water: 3–5 | Air: 3–5 | Time: 10–20 seconds |
|---|---|---|---|

The laser fibre is always held parallel to the root surface.

Increase in power is correlated with increase water and air irrigation which protects the root surface and the pulp from thermal damages during laser firing. Such laser therapy provides successful long term decrease of tooth hypersensitivity in periodontal patients.

Example 4

EVALUATION OF TREATMENT OF PERIODONTAL POCKETS WITH LASER

Introduction

In Periodontics the majority of treatments used for the control of supra- and subgingival microflora is provided by scaling and root planing. This mechanical therapy has been successfully used not only for the treatment of periodontal disease, but also for the maintenance of the treatment outcome on a long term basis (Badersten et al. 1981, Pihlstrom et al. 1983, Ramfjord et al. 1987). Scaling and root planing, however, is not always efficient in removal of all bacterial deposits and hard concrements from the diseased root surface, which may favour bacterial recolonisation of the periodontal pockets, thus leading to the recurrence of the disease (Rabbani et al. 1981, Stambaugh et al. 1981, Caffesse et al. 1986, Sherman et al. 1990).

In a number of studies the efficacy of mechanical therapy has been compared to that of systemic administered antibiotics (Listgarten et al. 1978, Quee et al. 1987), or local application of antibiotics alone (Ainamo et al. 1992, Pedrazzoli et al. 1992, Goodson et al. 1991) or antimicrobials in conjunction with scaling and root planing (Lindhe et al 1983, Mombelli et al. 1989, Magnusson et al. 1989). Theses studies indicated that administration of systemic or local antibiotics resulted in successful clinical outcomes. However, the risk of bacterial resistance to antimicrobials may restrict the use of this type of treatment only for specific situations.

Example 4

EVALUATION OF TREATMENT OF PERIODONTAL POCKETS WITH LASER

Introduction

In Periodontics the majority of treatments used for the control of supra- and subgingival microflora is provided by scaling and root planing. This mechanical therapy has been successfully used not only for treatment of periodontal disease, but also for maintenance of the therapy outcome on the long term (Badersten et al 1981, Lindhe et al. 1983, Pihlstrom et al. 1983, Ramfjord 1987). Scaling and root planing, however, is not always efficient in removal of hard concrements from the diseased root surface, which may favour bacterial recolonisation, thus leading to tile disease recurrence (Stambaugh et al. 1981, Caffese et al. 1986, Sherman et al. 1990).

In a number of studies the efficacy of mechanical therapy has been compared to that of systemic antibiotics (Listgarten et al. 1978, Quee et al. 1987), local antibiotics (Aimano et al. 1992, Pedrazzoll et al. 1992, Goodsen et al. 1992) or antimicrobials in conjunction with scaling and root planing (Lindhe et al 1983, Mombelli et al., 1989, Magnusson et al. 1989). Also theses studies indicated that administration of systemic or local antibiotics favoured clinical outcomes, the risk of bacterial resistance to antimicrobials restricts their use only for specific patients or sites. Thus, it required a search for a therapy which is efficient in improvement of periodontal parameters, when used alone or in combination with mechanical treatment.

Recently it has been suggested that short-duration pulsed Nd:YAG lasers have a potential for application in soft tissue-removal procedures due to minimal bleeding during surgery, which improves visibility to the operator and decreases surgery time. Pain and postsurgical complications are rare (Epstein 1991, Roshkind 1991, White et al. 1991). This type of laser needs a considerably less amount of generated heat, thus limiting collateral damages in the tissues adjacent to the treated area. Laser energy vaporise organical debris, including plaque and calculus, thus providing their efficient removal (for review see Myers 1991, Midda & Renton-Harper 1991, Midda 1992). Several in vitro and in vivo studies have shown a significant reduction or eradication of the putative pathogens adherent to root and calculus surfaces following local application of Nd:YAG laser (Tseng & Liew 1990, Tseng et al. 1991, White et al. 1991, Cobb et al 1991). Few SEM observations, however, indicated that Nd:YAG laser induced root surface alterations, which directly related to the energy level or exposure time (Cobb et al. 1991, Morlock et al. 1992, Trylovich et al. 1992), Thus, contradictory information exists regarding the application of lasers in the subgingival environment. Recently, new types of Nd:YAG laser has been developed which contains water and air irrigation for prevention of overheating and tissue alteration in tissues, adjacent to the target area. To date, there are no clinical studies evaluating the effect of subgingival curettage with this type of Nd:YAG laser.

The purpose of this study was to compare the effect of the subgingival treatment with laser versus scaling or combined laser/scaling therapy in adult patients with moderate or sever periodontitis.

Material and Methods

Experimental Design

The study was carried out as a single blind, randomised clinical trial, comparing the efficacy of three subgingival treatments: scaling (S-group), laser (L-group) and laser followed by scaling (L/S-group) versus each other and untreated control (C-group). A split mouth design was used, i.e. each patient received one of the three treatments randomly assigned to one of the three quadrants of the mouth whereas the last quadrant served as untreated control.

Patients Criteria 15 patients (8 males and 7 females), ranging in age from 34 to 74 years (mean 49) with evidence of moderate to severe periodontitis were selected for the study. Each patient presented at least two teeth in each of 4 quadrants with a pocket, depth 5 mm in at least one of 4 sites of each tooth, except for third molars. Exclusion criteria included mechanical and antibiotic therapy within last 3 months, localised juvenile periodontitis and compromised systemic condition. Each patient signed an informed consent.

Clinical Monitoring

At the initial examination (1 months prior to base line) the probing pocket depth (PPD) was recorded at 4 sites of each tooth: mid-buccal, mid-oral, distal and mesial (interproximally, a site with the greatest PPD buccally or lingually was chosen). PPD was measured to the nearest millimeter, using a coded Hu-Friedy PCP 12, with a 0.4 mm tip diameter and 1 mm graduations from the gingival margin to the tip of the probe when placed in the pocket The sites with furcation involvement were excluded. All subjects, who fulfilled the inclusion criteria were selected for the study. At this examination they received full mouth supragingival scaling, polishing and oral hygiene instruction.

At baseline, all sites with PPD 4 mm were treated and used for evaluation of pockets distribution within the groups prior and after treatment However, only the sites with PM>4 mm were determined as the experimental sites for evaluation of changes in pocket depth clinical attachment level (CAL) and proportions of sites with plaque (PL) and bleeding on probing (BOP). CAL was recorded from the cemento-enamel junction or a top of the tooth crown to the tip of the probe when placed in the pocket. Plaque accumulation (1: presence of plaque, otherwise 0), bleeding on probing (1: if bleeding appeared within 10 seconds after probing, otherwise 0) were recorded at the 4 sites of all teeth. All registrations were performed at baseline, 1 and 3 months post therapy by one investigator (JJ), who was unaware of the type of treatment assigned for each quadrant.

Treatment

At baseline, two randomly chosen quadrants received laser treatment, followed by scaling in one of those. The third quadrant was scaled, while the last quadrants was not treated. 1 months after, sites with bleeding on probing received a repeated treatment, assigned to the specific quadrant. Laser treatment was carried out using the following parameters average power—4.25 W, water spray-setting 7, air spray-setting 3, frequency—60 Hz, pulse width—250 $\mu$sec, duty cycle—30 sec per site. Laser treatment was effected by slow insertion of the optic fibre, aligned parallel to the root surface into a pocket while activating the laser. This resulted in gradual and painless placement of the fibre to the bottom of the pocket. The optic fibre was then slowly withdrawn from the pocket while activating the laser. Each site was treated for 30 seconds. All treatments were performed by one investigator (NL).

Statistical Method

Proportions of the sites with PL per quadrant were calculated out of total number of experimental sites in the quadrant. Proportions of the sites with BOP per quadrant were calculated out of total number of experimental sites in the quadrant.

The effect of each treatments was evaluated by comparing the mean change in PPD and CAL at 1 and 3 months versus the baseline measurements by means of the paired t-test.

Comparisons of efficacy of the 4 treatment regimes were based on average chance in pocket depths and attachment levels in each quadrant from baseline to 1 and 3 months and were evaluated by the paired t-tests.

Proportion of the sites with PL, BOP and % of pockets with PPD<4, 4–6 and >6 mm were calculated in each quadrant at 0, 1 and 3 months and compared by the paired t-tests. The significance level is chosen as $\alpha=0.05$ in all tests.

Results

All treatments were uneventful in all patients during the follow-up.

Table 1 presents the mean values for clinical parameters recorded at baseline. No statistically significant differences were observed in the proportions of sites with plaque and bleeding on probing, mean PM and pockets distribution within the treatment groups (all p>0.05). At 1 month, the proportions of sites exhibiting plaque were decreased versus baseline in all groups, however, the statistically significant difference was found only in the C-group (0.42 to 0.24) (FIG. 1). At 3 months post therapy, the reduction in number of sites with plaque was not statistically significant (p>0.05) in all groups.

Figure 2:
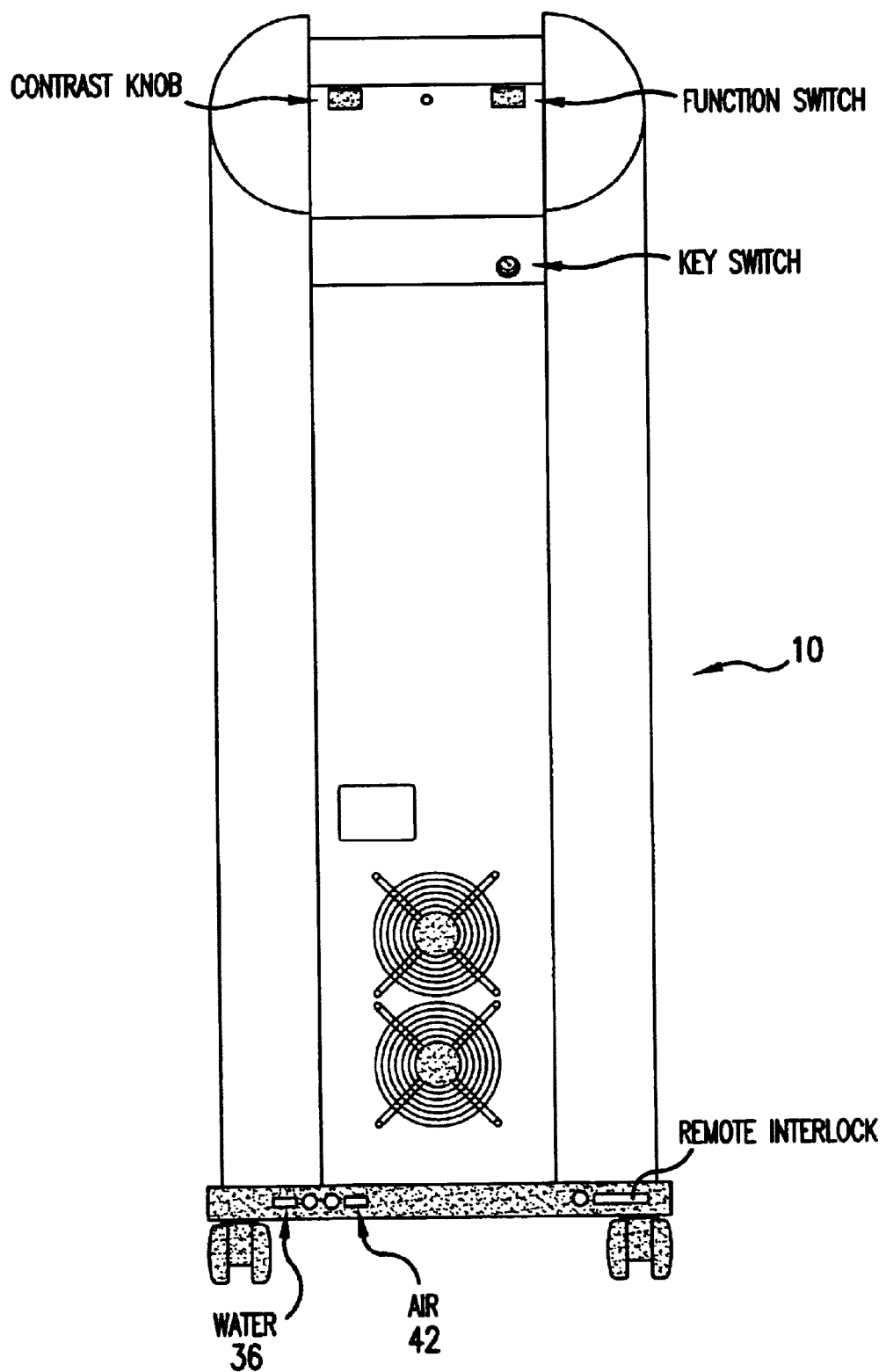
FIG. 2 is a rear view of a system shown in FIG. 1.
Figure 3:
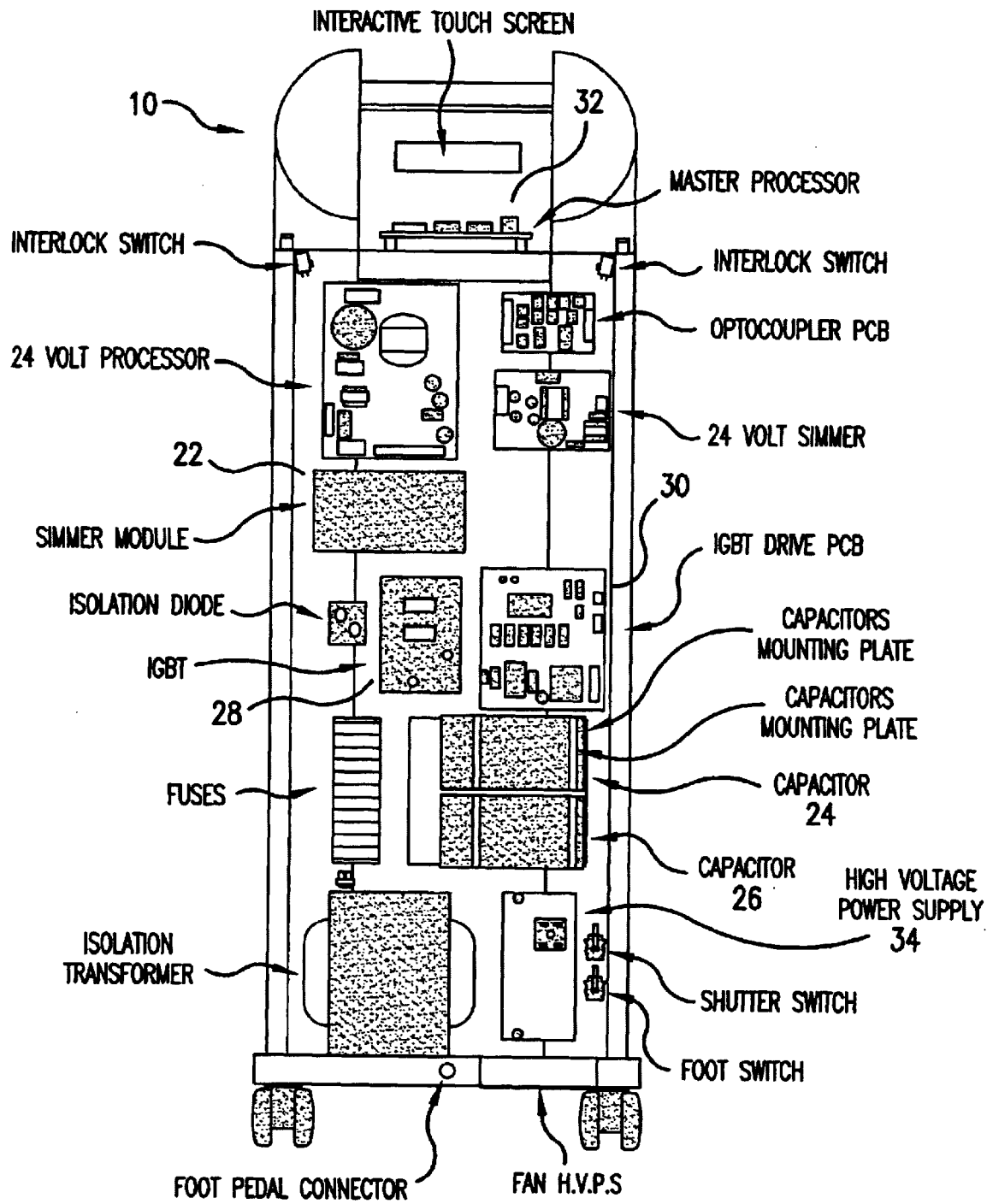
FIG. 3 is a front schematic of the system shown in FIG. 1 without cover plates.
Figure 4:
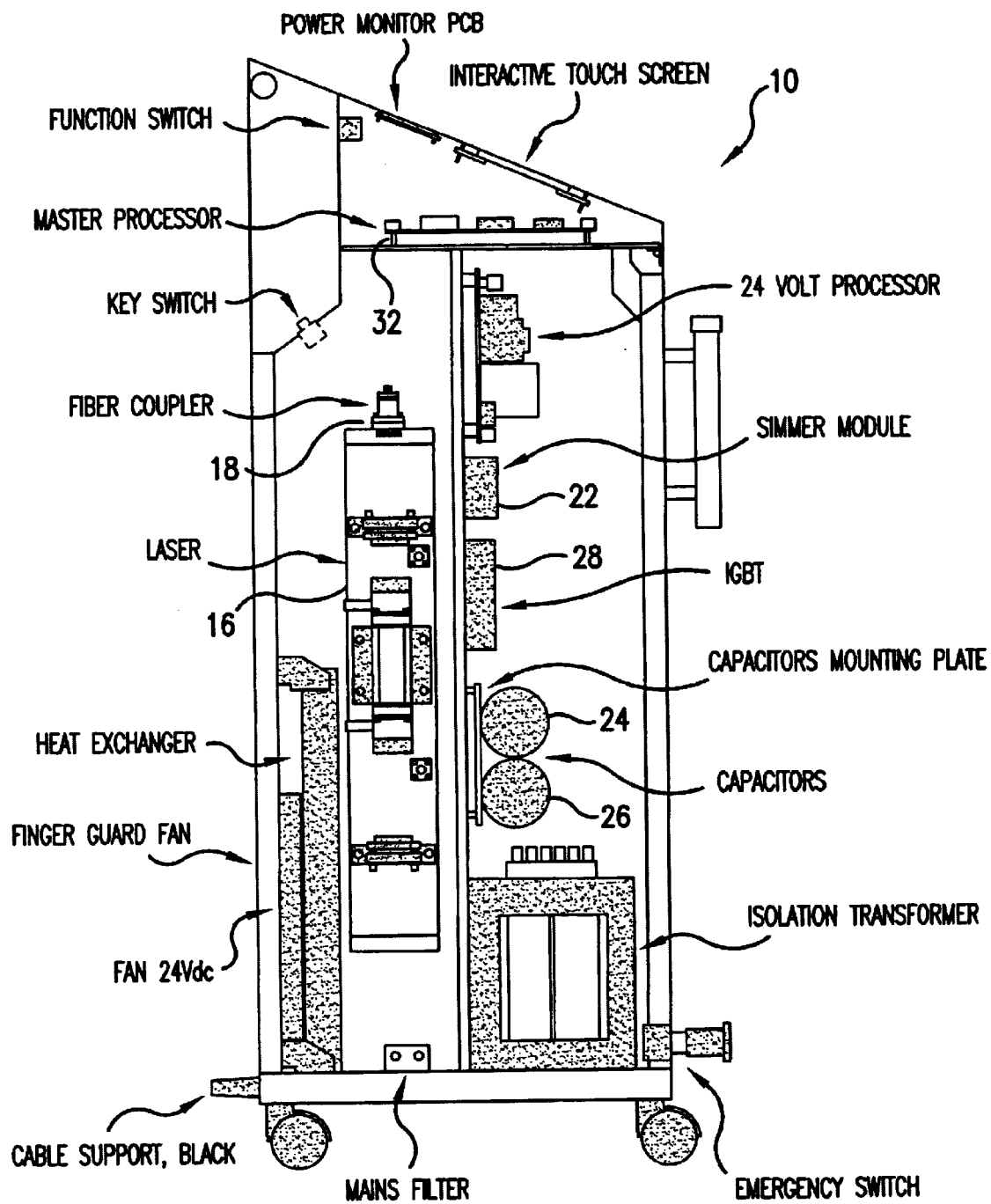
FIG. 4 is a side schematic of the system shown in FIG. 1 without cover plates.
Figure 5:
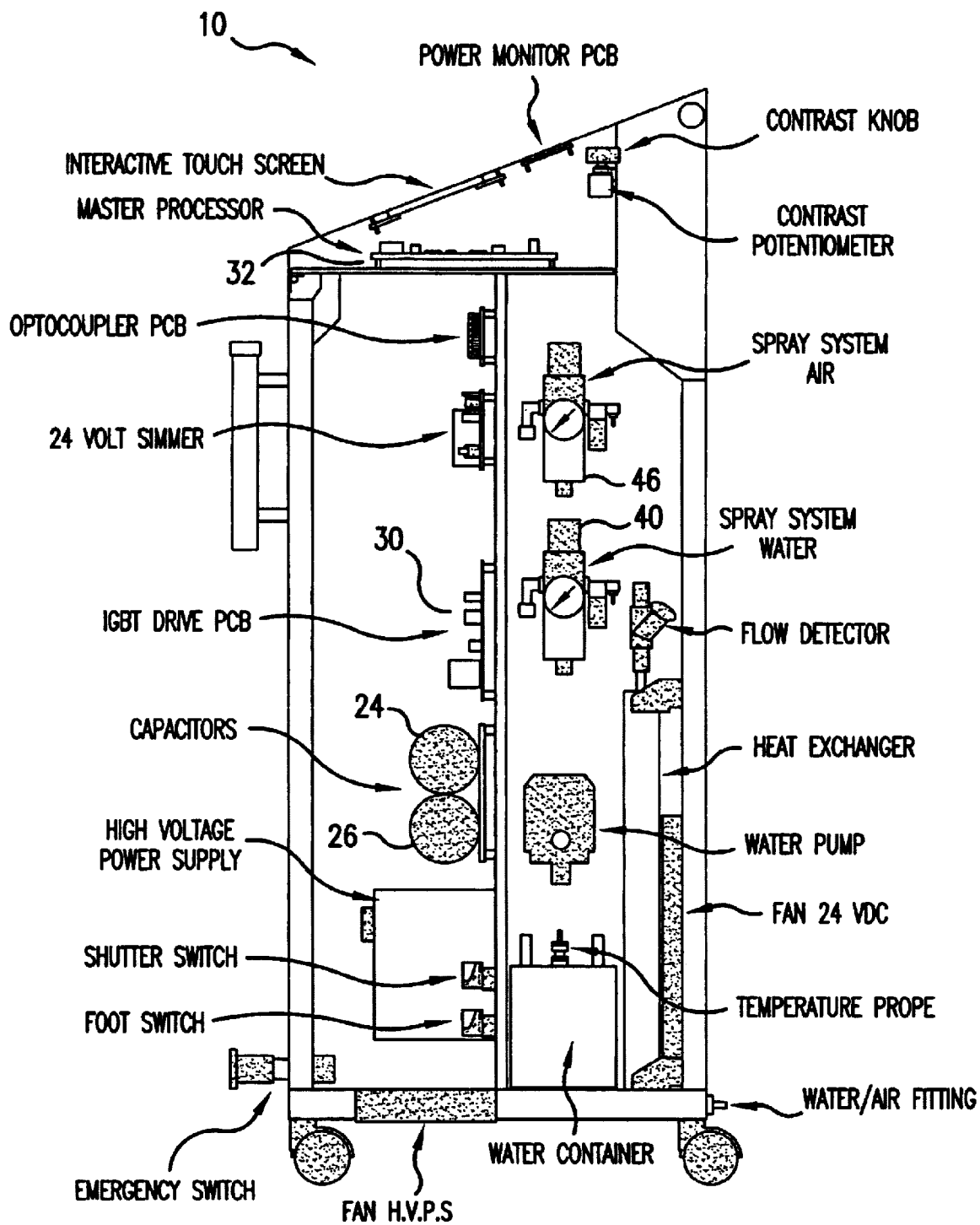
FIG. 5 is another side schematic of the system shown in FIG. 1 without cover plates.

The proportions of sites with bleeding on probing were significantly smaller after laser therapy alone (0.69 to 0.41) or in combination with scaling (0.67 to 0.40) at 1 month versus baseline (FIG. 2). The S-group presented less sites with BOP (0.57) than the C-group (0.66), however, significantly more than the L-group or the US-group. Thus, significantly more sites received repeated seating than other therapies at this observation period. At 3 months, the proportions of sites exhibiting BOP were significantly lower in all groups versus the baseline.

All treatments resulted in significant pocket depth reduction from 0 to 1 month in comparison with the non treatment, with the highest change of 0,97 mm in the sites subjected to laser/scaling therapy (Table 2). However, the statistically significant reduction in PP13 from 0 to 3 months was found only in the sites treated with the combined therapy. No difference was found in PPD-reduction between 0–1 and 0–3 months in any groups.

Statistically significant CAL gain from the baseline to 1 months was observed in the scaling (0.55 mm) and laser/scaling group (0.91 mm) versus the control group (0.48 mm) (Table 2). At.3 months, small non statistically significant CAL-gain (range 0.34–0.57 mm) was found in all groups versus the baseline (Table 2).

The % of pockets <4 mm, which did not exist at baseline, was significantly greater in all treatment groups versus the control 1 month post therapy. However, at 3 months, only the US-group and S-group contained significantly more shallow pockets than the C-group. The reduction of the % of deep >6 mm pockets was significant following the laser/scaling or laser therapy at 1 month Prom the baseline, and following the combined therapy or scaling at 3 months. Gradual reduction in the % of pockets 4–6 mm was found in all 4 groups at 1 and 3 months from the baseline.

At the end of the treatment phase, on the question regarding the preferable treatment all patients have chosen the laser therapy.

Discussion

The results of this randomised single blind controlled clinical trial indicated that laser treatment demonstrated similar to scaling effect on improvement of all clinical parameters in moderate and deep periodontal pockets. The mean change in PM in the laser treated sites was 0.76 and 0.79 mm at 1 and 3 months post therapy what was slightly higher than 0.62 and 0.70 mm achieved following scaling. Similarity in terms of CAL-gain was also observed between the laser treatment (0.68 and 0.54 mm) and scaling (0.55 and 0.54 min) at 1 and 3 months follow-up. These values agree with the data from several studies, evaluating the effect of subgingival scaling (Cercek et al. 1983, Ramfjord et al. 1987, Haffajee et al. 1997) or systemic or local antimicrobials (Listgarten, et al. 1978, Lindhe et al. 1983, Wennström et al. 1987, Eckles et al. 1990, Ainamo et al. 1992) on clinical improvement of pocket depth and attachment level. Both treatments resulted in a similar decrease of the percentage of deep pockets or sites with plaque, and an increase of percentage of shallow pockets after 1months, while at 3 months, scaling was more efficient in improving of those parameters. This, however, may be explained by a greater number of sites subjected to repeated scaling at 1 months due to bleeding on probing. Thus, laser therapy was more efficient in reduction of BOP, a risk factor for future attachment loss and disease progression (Lang et al. 1989, 1990), than scaling 1 month post treatment. This observation is not surprising due to antimicrobial effect of Nd:YAG laser, shown in studies in vitro and in vivo (Tseng et al. 1991a, White et al. 1991, Cobb et al. 1992). Obviously, In the present study the combined laser/scaling therapy was most beneficial ill decrease of PPD (0.97 and 0.99 mm) and CAL (0.91 and 0.57) 1 and 3 months post therapy. These results are supported by the data from an in vitro study by Tseng et al. (1991) and SEM study by Cobb et al. (1991) which demonstrated that laser therapy followed by scaling was more efficient in calculus removal from the periodontally involved root surface than laser done. Furthermore, the removal of lased calculus required significantly less strokes than non lased ones.

In addition, the changes in the clinical parameters observed post laser/scaling therapy are in accordance with those reported following scaling supplemented with local antimicrobials in other studies (Nakagawa et al. 1991, van Steenberghe et al. 1993, Newman et al. 1994). However, the results of the present study disagree with the findings from the investigation by Radvar et al (1990) in which Nd:YAG laser failed to improve clinical parameters of periodontal disease.

Several in vitro or SEM studies indicated that treatment of the root surface with laser may induce surface alteration, related to the time of exposure and energy levels (Cobb et al. 1992, Morlock et al. 1992, Trylovich et at. 1992). The Nd:YAG laser used in the present study contained water and air irrigation which in combination with a low exposure time (30 s per site) reduced the overheating of the subgingival tissues during laser activation. No complications have been observed post treatment and most of the patients experienced no or minimal pain which was lower than following scaling.

A reversal in the CAL-gain observed at 3 months in all treatment groups may most likely be explained by the absence of the professional oral hygiene control throughout the study. The predominate number of moderate 5 mm pockets, found in this study at baseline, may also have influenced the values of PPD and CAL-reduction. The pattern of low attachment level gain at sites with a moderate initial pocket depth has been previously described (Pihistr öm et al., 1983, Ramfjord et al, 1987).

In conclusion, the data of this study revealed: 1) Nd:YAG laser showed similar to scaling effect in treatment of moderate and deep periodontal pockets; 2) combined laser and scaling therapy resulted in most beneficial improvement of all clinical parameters. However, histological investigations evaluating the effect of this type of laser have yet to be conducted.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A dental system for laser gingivectomy of periodontal pockets, comprising:
    a handpiece for directing laser light and a coolant spray towards a target tissue area to be surgically treated; said handpiece comprising:
        a housing with an input end and an output end;
        an optical fiber duct for receiving and holding an optical fiber and extending within the housing from the input end to the output end;
        an optical fiber positioned in the optical fiber duct and having a fiber output end for emission of the laser light;
        a seal positioned in the optical fiber duct and adapted to receive and hold the optical fiber in water tight engagement with the optical fiber duct;
        an air duct for transmission of compressed air and extending within the housing from the input end to the output end; and
        a water duct for transmission of water and extending within the housing from the input end and being interconnected with the optical fiber duct within the housing between the output end and the seal so that water flowing in the water duct leaves the housing at the output end through the optical fiber duct; and an apparatus, said apparatus comprising:
        a laser for emission of laser light into the optical fiber, the laser being adapted to perform laser gingivectomy in that it has a wavelength ranging from 1.06 $\mu$m to 1.07 $\mu$m and emits light pulses having a duration ranging from 200 $\mu$s to 300 $\mu$s at a repetition rate ranging from 55 Hz to 65 Hz and having intensities giving an average power ranging from 1 W to 10 W;
        a water control member adapted to be interconnected between a water supply and the water duct and to control the amount of water flowing into the water duct;
        an air control member adapted to be interconnected between a supply of compressed air and the air duct and to control the amount of compressed air flowing into the air duct; and
        a controller for controlling the operation of the system and being connected to the water control member and the air control member and being adapted to set the amount of water flowing into the water duct in the range from 5 ml/min to 50 ml/min and to set the pressure of compressed air flowing into the air duct so that a coolant spray of mixed air and water is formed whereby efficient cooling of tissue surrounding target tissue being cut by the laser light is provided.

2. The system according to claim 1, wherein the controller is adapted to set the amount of water flowing into the water duct in the range from 10 ml/min to 30 ml/min.

3. The system according to claim 1, wherein the controller is adapted to set the amount of water flowing into the water duct to approximately 20 ml/min.

4. The system according to claim 1, wherein the laser is adapted to emit light pulses with a repetition rate of approximately 60 Hz.

5. The system according to claim 1, wherein the laser is adapted to emit light pulses with a pulse duration of approximately 250 $\mu$s.

6. The system according to claim 1, wherein the laser is adapted to emit light pulses with an average power ranging from 3 W to 8 W.

7. The system according to claim 6, wherein the laser is adapted to emit light pulses with an average power ranging from 4 W to 6 W.

8. The system according to claim 7, wherein the laser is adapted to emit light pulses with an average power of approximately 5 W.

9. The system according to claim 6, wherein the laser is adapted to emit light pulses with an average power ranging from 5 W to 8 W.

10. The system according to claim 9, wherein the laser is adapted to emit light pulses with an average power ranging from 6 W to 7 W.

11. The system according to claim 1, wherein the laser is adapted to emit light for a period ranging from 10 s to 1 minutes upon user activation.

12. The system according to claim 11, wherein the laser is adapted to emit light for a period ranging from 20 s to 50 s upon user activation.

13. The system according to claim 12, wherein the laser is adapted to emit light for a period of approximately 30 s upon user activation.

14. The system according to claim 1, wherein the controller comprises a timer for accumulation of the time during which light has been emitted by the system.

15. A dental method for gingivectomy of periodontal pockets, comprising the steps of:

emitting laser light from an optical fiber held in a handpiece, the laser light being adapted to perform laser gingivectomy in that it has a wavelength ranging from 1.06 $\mu$m to 1.07 $\mu$m into the optical fiber, it is emitted in pulses having a pulse duration ranging from 200 $\mu$s to 300 $\mu$s at a repetition rate ranging from 55 Hz to 65 Hz and having intensities giving an average power ranging from 1 W to 10 W;

emitting a coolant spray of water and air from the handpiece in the direction of the emitted laser light by transmission of compressed air and water in the handpiece along the optical fiber, the amount of water flowing along the optical fiber being in the range from 5 ml/min to 50 ml/min, the pressure of compressed air flowing along the optical fiber being adjusted so that a coolant spray of mixed air and water is formed; and directing the emitted laser light and the coolant spray towards a target tissue area to be cut whereby efficient cooling of tissue surrounding target tissue being cut by the laser light is provided.

16. A method of laser curettage of periodontal pockets, comprising the steps of:

emitting laser light from an optical fiber held in a handpiece;

emitting a coolant spray of water and air from the handpiece in the direction of the emitted laser light by transmission of compressed air and water in the handpiece along the optical fiber, the amount of water flowing along the optical fiber being in the range from 5 ml/min to 50 ml/min, the pressure of compressed air flowing along the optical fiber being adjusted so that a coolant spray of mixed air and water is formed; and directing the emitted laser light and the coolant spray towards a target tissue area to be treated whereby efficient cooling of tissue surrounding target tissue being treated by the laser light is provided, wherein the optical fiber is maintained in a substantially parallel position to the root of the tooth under treatment, the method further comprising the steps of:

positioning of the optical fiber in contact with epithelium at the entrance to the pocket to be treated;

inserting the fiber into the pocket by moving the fiber in the bucco-lingual direction in proximal sites and in the mesio-distal direction in buccal or lingual sites;

moving the fiber in contact with the soft tissue apically to the bottom of the pocket and into contact with the root surface whereby pocket epithelium and granulation tissue are removed and the root surface is disinfected; and withdrawing the fiber coronally from the pocket.

17. A method of laser surgery on periodontal pockets, comprising the steps of:

emitting laser light from an optical fiber held in a handpiece;

emitting a coolant spray of water and air from the handpiece in the direction of the emitted laser light by transmission of compressed air and water in the handpiece along the optical fiber, the amount of water flowing along the optical fiber being in the range from 5 ml/min to 50 ml/min, the pressure of compressed air flowing along the optical fiber being adjusted so that a coolant spray of mixed air and water is formed; and directing the emitted laser light and the coolant spray towards a target tissue area to be treated whereby efficient cooling of tissue surrounding target tissue being treated by the laser light is provided, wherein the optical fiber is maintained in a substantially horizontal position during treatment, the method further comprising the steps of:

identifying depth and type of the pocket to be treated;

incising the fiber superficially at the bottom of the pocket to be treated;

moving the fiber through the gingiva; and removing excised tissue with a curette or pincer.

18. The method according to claim 17, further comprising, at interproximal sites, the steps of:

moving the fiber through the gingiva at buccal and oral aspects;

lifting loose tissue with a pincer or curette;

separating loose tissue from the interdental periodontium with the fiber; and disinfecting the exposed root surface with the laser light.

19. A method of laser surgery on periodontal pockets, comprising the steps of emitting laser light from an optical fiber held in a handpiece;

emitting a coolant spray of water and air from the handpiece in the direction of the emitted laser light by transmission of compressed air and water in the handpiece along the optical fiber, the amount of water flowing along the optical fiber being in the range from 5 ml/min to 50 ml/min, the pressure of compressed air flowing along the optical fiber being adjusted so that a coolant spray of mixed air and water is formed; and directing the emitted laser light and the coolant spray towards a target tissue area to be treated whereby efficient cooling of tissue surrounding target tissue being treated by the laser light is provided, wherein the optical fiber is maintained in a substantially 45° angle in relation to a longitudinal axis of the tooth to be treated, the method further comprising the steps of:

gradually incising the fiber towards the bottom of the pocket while dissecting; and removing the granulation tissue and pocket epithelium with a curette.

20. A method of laser furcation treatment of periodontal pockets, comprising the steps of emitting laser light from an optical fiber held in a handpiece;

emitting a coolant spray of water and air from the handpiece in the direction of the emitted laser light by transmission of compressed air and water in the handpiece along the optical fiber, the amount of water flowing along the optical fiber being in the range from 5 ml/min to 50 ml/min, the pressure of compressed air flowing along the optical fiber being adjusted so that a coolant spray of mixed air and water is formed; and directing the emitted laser light and the coolant spray towards a target tissue area to be treated whereby efficient cooling of tissue surrounding target tissue being treated by the laser light is provided, the method further comprising the steps of:

horizontally incising the fiber to the base of the pocket under treatment;

removing the dissected soft tissue flap;

vaporizing the remaining granulation tissue in the furcation defect; and disinfecting the root surface with laser light.

21. A method of laser furcation treatment of periodontal pockets, comprising the steps of emission of laser light from an optical fiber held in a handpiece, emission of a coolant spray of water and air from the handpiece in the direction of the emitted laser light by transmission of compressed air and water in the handpiece along the optical fiber, the amount of water flowing along the optical fiber being in the range from 5 ml/min to 50 ml/min, the pressure of compressed air flowing along the optical fiber being adjusted so that a coolant spray of mixed air and water is formed, and directing the emitted laser light and the coolant spray towards a target tissue area to be treated whereby efficient cooling of tissue surrounding target tissue being treated by the laser light is provided, the method further comprising the steps of:

horizontally incising the fiber to the base of the pocket in the buccal site of the tooth under treatment;

horizontally incising the fiber to the base of the pocket in the lingual site of the tooth under treatment;

removing soft tissue flaps by horizontal intracrevicular incisions at both sites;

excising granulation tissue in the furcation by horizontal incision of the fiber; and removing granulation tissue with a pincer or curette.

* * * * *